United States Patent [19]
Cook et al.

[11] Patent Number: 5,914,396
[45] Date of Patent: Jun. 22, 1999

[54] 2'-O-MODIFIED NUCLEOSIDES AND PHOSPHORAMIDITES

[75] Inventors: Phillip Dan Cook, San Marcos; Charles John Guinosso, Vista, both of Calif.

[73] Assignee: ISIS Pharmaceuticals, Inc., Carlsbad, Calif.

[21] Appl. No.: 08/373,298

[22] PCT Filed: Jul. 20, 1993

[86] PCT No.: PCT/US93/06807

§ 371 Date: Feb. 22, 1995

§ 102(e) Date: Feb. 22, 1995

[87] PCT Pub. No.: WO94/02501

PCT Pub. Date: Feb. 3, 1994

Related U.S. Application Data

[62] Continuation-in-part of application No. 07/968,849, Oct. 30, 1992, abandoned, application No. 07/777,670, Oct. 15, 1991, Pat. No. 5,212,295, application No. 08/058,023, May 5, 1993, Pat. No. 5,521,302, application No. PCT/US91/00243, Jan. 11, 1991, and application No. 08/244,993, filed as application No. PCT/US92/11339, Dec. 23, 1992, Pat. No. 5,623,065, which is a continuation-in-part of application No. 07/814,961, Dec. 24, 1991, abandoned, said application No. 07/968,849, is a continuation-in-part of application 07/967,267, Oct. 27, 1992, which is a continuation-in-part of application No. 07/918,362, Jul. 23, 1992, Pat. No. 5,506,351, which is a continuation-in-part of application No. 07/463,358, Jan. 11, 1990, abandoned, and application No. 07/566,977, Aug. 13, 1990, abandoned.

[51] Int. Cl.$^6$ ............... C07H 19/067; C07H 19/167; C07H 21/02; C07H 19/10
[52] U.S. Cl. ............... 536/26.1; 536/24.5; 536/27.1; 536/28.1
[58] Field of Search ............... 536/24.5, 24.3, 536/27.1, 28.1, 26.1; 514/44

[56] References Cited

U.S. PATENT DOCUMENTS

| | | | |
|---|---|---|---|
| 3,687,808 | 8/1972 | Merigan, Jr. et al. | 195/28 |
| 4,415,732 | 11/1983 | Caruthers et al. | 536/27 |
| 4,458,066 | 7/1984 | Caruthers et al. | 536/27 |
| 4,500,707 | 2/1985 | Caruthers et al. | 536/27 |
| 4,668,777 | 5/1987 | Caruthers et al. | 536/27 |
| 4,725,677 | 2/1988 | Koster et al. | 536/27 |
| 5,013,830 | 5/1991 | Ohtsuka et al. | 536/27 |
| 5,034,506 | 7/1991 | Summerton et al. | 528/391 |
| 5,214,135 | 5/1993 | Srivastava et al. | 536/26.7 |
| 5,466,786 | 11/1995 | Buhr et al. | 435/26.26 |

FOREIGN PATENT DOCUMENTS

| | | |
|---|---|---|
| 2017369 | 11/1990 | Canada . |
| 0260032 | 3/1988 | European Pat. Off. . |
| 0287313 | 10/1988 | European Pat. Off. . |
| 0378518 | 7/1990 | European Pat. Off. . |
| 0399330 | 11/1990 | European Pat. Off. . |
| 0417999 | 3/1991 | European Pat. Off. . |
| 3915462 | 9/1990 | Germany . |
| 4110085 | 10/1992 | Germany . |
| WO 90/08156 | 7/1990 | WIPO . |
| WO 91/06556 | 5/1991 | WIPO . |
| WO 91/15499 | 10/1991 | WIPO . |
| WO 92/02534 | 2/1992 | WIPO . |
| WO 92/05186 | 2/1992 | WIPO . |
| 0519463 A1 | 12/1992 | WIPO . |

OTHER PUBLICATIONS

Beaucage, S. and Caruthers, M., "Doexynucleoside phosphoramidites—A new class of key intermediates for deoxypolynucleotide synthesis", *Tetrahedron Letters,* 22:1859–1862 (1981).

Berner, S. et al., "Studies on the Role of Tetrazole in the Activation of Phosphoramidites", *Nucleic Acids Research* 17:853–864 (1989).

Caruthers, M., "Synthesis of Oligonucleotides and Oligonucleotide Analogues", in "Oligonucleotides. Antisense Inhibitors of Gene Expression.", J.S. Cohen, ed., *CRC Press, Inc.,* 7–24, (1989).

Chang, Chi–Deu and Coward James K., "Analogues of S–Adenosylhomocysteine as Potential Inhibitors of Biological Transmethylation. Synthesis of Analogues with Modifications at the 5'–Thioether Linkage", *Journal of Medicinal Chemistry,* 19:5 684–691 (1976).

Cotten et al., "2'–O–methyl, 2'–O–ethyl, Oligoribonucleotides and phosphorothioate Oligodeoxyribinucleotides as inhibitors of the in vitro U7 snRPN–dependent mRNA processing event", *Nucleic Acids Research* 19:10 2629–2635, (1991).

Dahl, B.H., et al., "Mechanistic studies on the phosphoramidite coupling reaction in oligonucleotide synthesis. I. Evidence for nucleophilic catalysis by tetrazole and rate variations with the phosphorus substituents", *Nucleic Acids Research,* 15:1729–1743 (1987).

Ekborg, G. and Garegg, P.J., "Synthesis of the 2'–O– and 3'–O–Methyl Ethers of Guanosine", *J. Carbohydrates, Nucleosides, Nucleotides* 7:57–61 (1980).

Gladkaya, V.A., et al., "Synthesis of N,O–Protected Derivatives of 2'–O Methylcytidine and of 2'–O–Methyl–and N$_1$–Methylguanosines", *Khim. Prir. Soedin.,* 4:568 (1989).

Guinosso, C.J., et al., "Synthesis and Biophysical and Biological Evaluation of 2'–Modified Antisense Oligonucleotides", *Nucleosides & Nucleotides,* 10:259–262 (1991).

Hansske, F., et al., "2' and 3'–Ketonucleosides and their Arabino and XYLO Reduction Products" Convenient Access VIA Selective Production and Oxidation of Ribonucleosides, *Tetrahedron,* 40:1 125–135 (1984).

Inoue, H., et al., "Synthesis and Properties of Nucleic Acid Probes", *Nuc. Acids Research* 16:165–168 (1985).

(List continued on next page.)

Primary Examiner—Gary L. Kunz
Attorney, Agent, or Firm—Woodcock Washburn Kurtz, Mackiewicz & Norris LLP

[57] ABSTRACT

2'-O-Modified nucleosides, nucleotides, and oligonucleotides. These 2'-O-modified oligonucleotides are resistant to nuclease digestion and can effectively hybridize to a complementary polynucleotide.

4 Claims, No Drawings

OTHER PUBLICATIONS

Inoue, H., et al., "Sequence–dependent hydrolysis of RNA using modified oligonucleotide splints and RNase H". *FEB Letters,* 215:2 327–330 (1987).

Inoue, H. et al., "Synthesis and hybridization studies on two complementary nona('2–O–methyl)ribonucleotides", *Nucleic Acids Research,* 15:15 6131–6148 (1987).

Iribarren, et al., "2'–O–Alkyl Oligonucleotides as Antisense Probes", *Proc. Natl. Acad. Sci.,* 87:7747–7751 (1990).

March, J., *Advanced Organic Chemistry,* Wiley–Interscience, John Wiley & Sons, New York, 220 (1985).

Nielsen, J., et al., "Thermal Instability of Some Alkyl Phosphorodiamidites", *J. Chem. Research* 26–27 (1986).

Nielsen, P.E., et al., "Sequence–Selective Recognition of DNA by Strand Displacement with a Thymine–Substituted Polyamide," *Science 254:*1497–1500 (1991).

Robins, M.J., et al., "Nucleic Acid Related Compounds. 12. The Facile and High–Yield Stannous Chloride Catalyzed Monomethylation of the Cis–Glycol System of Nucleosides by Diazomethane" *J. Org. Chem.,* 39:13 1891–1899 (1974).

Robins et al., "Nucleic Acid related compounds. 36. Synthesis of the 2'–O–methyl and 3'–O–methyl ethers of guanosine and 2–aminoadenosine and correlation of O'–methylnucleoside $_{13}$C nmr special shifts", *Can. J. Chem.,* 59:3360–3364 (1981).

Singer, et al., "Alkylation of Ribose in RNA Reacted with Ethylnitrosourea at Neutrality" *Biochemistry* 15:5052–5057 (1976).

Sproat, B.S., et al., "New synthetic routes to protected purine 2'–O–methylriboside–3'–O–phosphoramidites using a novel alkylation procedure", *Nucleic Acids Research* 18:1 41–49 (1990).

Sproat, B.S., et al. "2'–O–Methyloligoribonucleotides: synthesis and applications, Oligonculeotides and Analogs A Practical Approach", Eckstein, F. Ed.; *IRL Press,* Oxford, 46–86 (1991).

Sproat, B.S., et al., "New Synthetic routes to Synthons Suitable for 2'O–Allyl–Oligoribonucleotide Assembly", *Nucleic Acids Research,* 19:4 733–738 (1991).

Sproat, B.S., et al., "2'–O–Alkyloligoribonculeotides: Synthesis and Applications in Studying RNA Splicing", *Nucleotides & Nucleosides,* 10:25–35 (1991).

Wagner, D., et al., "Preparation and Synthetic Utility of Some Organotin Derivatives of Nucleosides", *J. Org. Chem. 39:*24–30 (1974).

Wagner, E., et al., "A simple procedure for the preparation of protected 2'–O–methyl or 2'–O–ethyl ribonucleoside–3'–O–phosphoramidites", *Nucleic Acids Research,* 19:21 5965–5971 (1991).

Yamauchi, K., et al., "Methylation of Nucleosides with Trimethylsulfonium Hydroxide. Effects of Transition metal Ions", *J. Org. Chem.,* 45:3865–3868 (1980).

Zon, G. and Stec, J., "Phosphorothioate Oligonucleotides: Oligonucleotides and Analogs A Practical Approach"; Eckstein, F. Ed.; *IRL Press,* Oxford, (1991).

Keller et al., A General method for the Synthesis of 2'–O–Modified Ribonucleosides', *Helvetica Chimica Acta* 1993, 76, 884–892.

Chavis, C. et al., "Synthesis of 2',3'–Differentiated Ribonucleosides via Lycosylation Reactions with 2'–O–TBDMS Ribofuranose Derivatives. A. Pyrimidine Series", *J. Org. Chem.* 1982, 47, 202–206.

Divakar, K.J. et al., "Reaction Between 2,2'–Anhydro–1–β–p–arabinofuranosyluracil and Thiolate Ions", *J. Chem. Soc. Perkin Trans.* 1982, 1625–1628.

Heinemann, U. et al., "Effect of a Single e'–methylene Phosphonate Linkage on the Conformation of an A–DNA Octamer Double Helix", *Nucleic Acids Res.* 1991, 19(3), 427–433.

Morr, M. et al., "Building Blocks for the CHemical Synthesis of DNA Containing C(3')–CH$_2$–P Bonds", in "Chemical Synthesis in Molecular Biology", GBF (Gesellschaft fuer Biotechnologische Forschung Braunschweig–Stoeckheim), Bloecker et al, eds., 1987, vol. 8, pp. 107–113.

Singer, B. and Kusmierek, "Alkylation of Ribose in RNA Reacted with Ethylnitrosourea at Neutrality", *Biochemistry* 1976, 15(23), 5052–5057.

Wagner, D. et al., "Preparation and Synthetic Utility of Some Organotin Derivatives of Nucleosides", *J. Org. Chem.* 1974, 39(1), 24–30.

Chemical Abstracts, vol. 110, Jan. 24, 1989, Abstract No. 24,228; Kikuchi et al., Z. Naturforsch., B: Chem. Sci. 43(5):623–630, 1988.

2'-O-MODIFIED NUCLEOSIDES AND PHOSPHORAMIDITES

CROSS REFERENCE TO RELATED APPLICATION

This patent application is filed under 35 USC 371 of the National Stage of International Application of PCT/US93/06,807 filed on Jul. 20, 1993, which in turn is a continuation-in-part of U.S. application Ser. No. 07/968,849, filed on Oct. 30, 1992, now abandoned, which is a continuation-in-part of U.S. application Ser. No. 07/967,267, filed on Oct. 27, 1992, which is a continuation-in-part of U.S. application Ser. No. 07/918,362, filed on Jul. 23, 1992 (now U.S. Pat. No. 5,506,351). This application also is a continuation-in-part of U.S. application Ser. No. 07/777,670, filed on Oct. 15, 1991 (now U.S. Pat. No 5,212,295), U.S. application Ser. No. 08/058,023, filed on May 5, 1993 (now U.S. Pat. No. 5,521,302), U.S. application Ser. No. 08/244,993 filed Jun. 21, 1994 (now U.S. Pat. No. 5,623,065) which is a 371 of International Application PCT/US92/11339, filed on Dec. 23, 1992 (now U.S. Pat. No. 5,623,065), and International Application PCT/US91/00,243, filed on Jan. 11, 1991. International Application PCT/US91/00243 is a continuation-in-part of U.S. application Ser. No. 07/463,358, filed on Jan. 11, 1990, now abandoned, and U.S. application Ser. No. 07/566,977, filed on Aug. 13, 1990 now abanoned. International Application PCT/US92/11339 is a continuation-in-part of U.S. application Ser. No. 07/814,961, filed on Dec. 24, 1991 now abandoned. These patent applications are assigned to the assignee of the present patent application and are incorporated by reference herein in their entirety.

FIELD OF INVENTION

This invention is directed to processes for the preparation of 2'-O-alkyl uridine and cytidine phosphoramidites. This invention is also directed to processes for the preparation of 2'-O-alkyl, 3'-O-alkyl and 2',3'-di-O-alkyl 2,6-diaminopurine riboside, 2'-O-alkyl guanosine and 2'-O-alkyl guanosine analogs, phosphoramidites of these compounds and methods of use thereof.

BACKGROUND OF THE INVENTION

A number of oligonucleotide analogs have been made. One class of oligonucleotides that have been synthesized are the 2'-O-substituted oligonucleotides. Such oligonucleotides have certain unique and useful properties. In U.S. patent application Ser. No. 814,961, filed Dec. 24, 1991, now abandoned, entitled Gapped 2' Modified Phosphorothioate Oligonucleotides, assigned to the same assignee as this application, the entire contents of which are herein incorporated by reference, 2' substituted nucleotides are introduced within an oligonucleotide to induce increased binding of the oligonucleotide to a complementary target strand while allowing expression of RNase H activity to destroy the targeted strand.

In a recent article, Sproat, B. S., Beijer, B. and Iribarren, A., Nucleic Acids Research, 1990, 18:41, the authors noted further use of 2'-O-methyl substituted oligonucleotides as "valuable antisense probes for studying pre-mRNA splicing and the structure of spliceosomes".

2'-O-methyl and ethyl nucleotides and methods of making the same have been reported by a number of authors.

Robins, M. J., Naik, S. R. and Lee, A. S. K., J. Org. Chem., 39:1891 (1974) reported a low yield synthesis of 2'-O- and 3'-O-methyl guanosine via a stannous chloride catalyzed monomethylation by diazomethane. As was later reported by Robins, M. J., Hansske, F. and Bernier, S. E., Can. J. Chem., 59:3360 (1981), "convenient and high yield methods have been devised for synthesis of the 2'—O— and 3'-O-methyl ethers of adenosine, cytidine, and uridine . . . However, guanosine has presented significant difficulties." In the foregoing paper, the authors reported an improved synthesis of 2'-O and 3'-O-methyl guanosine. The synthesis was improved by effecting the stannous chloride catalyzed diazomethane methylation of 2,6-diamino-9-(β-D-ribofuranosyl)purine (2-aminoadenosine) in place of guanosine. The diamino purine moiety was then reduced to the corresponding guanine moiety with adenosine deaminase. In a further diazoation reaction described by Singer and Kusmierek, Biochemistry 15:5052 (1976), a mixture of 2' and 3'-O-ethyl guanosine was reported to result from the treatment of guanosine with diazoethane. The alkylation also resulted in alkylation of the heterocyclic base. The alkylated product was treated with base to remove the ethyl group from the heterocyclic base. The resulting product was identified by virtue of having the same UV spectrum as that of guanosine, but a Rf differing from the Rf of guanosine.

A further improvement in the synthesis of 2'-O-methyl nucleosides was reported by Inoue, H., Hayase, Y. Imura, A., Iwai, S., Miura, K. and Ohtsuka, E., Nucleic Acids Research, 15:6131 (1987). This method of synthesis was effected utilizing CH3I in the presence of $Ag_2O$. This method proved useful for all of the common nucleotides with the exception of guanosine. As reported by these authors, guanosine proved refractory to this synthetic method. Thus these authors again had to effect the 2'-O-methylation of guanosine with diazomethane. In order to avoid methylation of the amino functionality of the guanine base moiety, the guanine base moiety was blocked with an isobutyryl group. Additionally, to avoid methyl esterification of the 3'-O functionality of the sugar moiety, a TIPDS (tetraisopropyldisiloxane) blocking group was used to block both the 3' and the 5' hydroxyls of the sugar moiety.

Sproat et al., supra and Sproat, B. S., Iribarren, A. M., Garcia, R. G. and Beijer, B., Nucleic Acids Research, 19:733 (1991) addressed the synthesis of 2'-O-methyl guanosine (and 2'-O-allyl guanosine). In both of these Sproat et al. publications, the investigators presented a further synthetic pathway to 2'-O-methylguanosine and 2'-O-allylguanosine. They characterized the further pathway with respect to the prior known synthetic methods as "avoids(ing) . . . the use of the highly toxic and potentially explosive reagent diazomethane" and being "far superior to the use of silver oxide/methyl iodide." This same synthetic method of the Sproat et al. investigators is also published in B. S. Sproat and A. I. Lamond, "2'-O-Methyloligoribonucleotides: synthesis and applications," Oligonucleotides and Analogues, ed. F. Eckstein, (IRL Press, 1991) which described syntheses of 2'-O-methylribonucleoside-3'-O-phosphoramidites. The uridine phosphoramidite synthesis described therein requires both base and sugar protection of the starting nucleoside prior to alkylation. Only after the base and sugar protecting groups are in place on the uridine is it then alkylated. Post alkylation, the base protecting group is removed followed by 5'-O-dimethoxytritylation and phosphitylation. The cytidine phosphoramidite synthesis described by Sproat and Lamond utilizes (and thus requires) the base and sugar blocked 2'-O-methyl uridine analog. This analog is then converted to a blocked cytidine analog, the blocking group is removed from the sugar, the analog is dimethoxytritylated and finally phosphitylated. The guanosine phosphoramidite synthesis taught by Sproat and Lamond starts from a 2-amino-6-chloronucleoside having 3' and 5' sugar hydroxy groups blocked. This nucleoside is converted to a 2,6-dichloro derivative. The dichloro compound is then 2'-O-alkylated. Following O-alkylation, the dichloro compound is converted to a diazido intermediate. The diazido intermediate is in turn converted to a diamino intermediate. The diamino intermediate is then deaminated to the guanosine analogue. The 2-amino group of the guanosine analogue is blocked followed by dimethoxytritylation and finally phosphitylation. This guanosine procedure is also published in Sproat, et. al., *Nucleic Acids Research,* 1991 19:733.

The above synthetic procedures involve multiple steps and numerous reagent treatments—9 different reagent treatments for uridine, 10 for cytidine and 12 for guanosine. For the cytidine and guanosine compounds at least one of the reagents that is required is not readily available and thus is a very expensive reagent.

Other groups have taught the preparation of other 2'-O-alkylated nucleosides. 2'-O-methylthiomethylguanosine, was reported by Hansske, F., Madej, D. and Robins, M. J., *Tetrahedron,* 40:125 (1984). It was produced as a minor by-product of an oxidization step during the conversion of guanosine to 9-β-D-arabinofuranosylguanine, i.e. the arabino analogue of guanosine. The addition of the 2'-O-methylthiomethyl moiety is an artifact from the DMSO solvent utilized during the oxidization procedure. The 2'-O-methylthiomethyl derivative of 2,6-diaminopurine riboside was also reported in the Hansske et al. publication. It was also obtained as an artifact from the DMSO solvent.

In addition, Gladkaya, et al., *Khim. Prir. Soedin.,* 1989, 4, 568 discloses $N_1$-methyl-2'-O-(tetrahydropyran-2-yl) and 2'-O-methyl guanosine. Sproat, et al., *Nucleic Acids Research,* 1991, 19, 733 teaches the preparation of 2'-O-allyl-guanosine. Allylation of guanosine required a further synthetic pathway. Iribarren, et al., *Proc. Natl. Acad. Sci.,* 1990, 87, 7747 also studied 2'-O-allyl oligoribonucleotides. Iribarren, et al. incorporated 2'-O-methyl-, 2'-O-allyl-, and 2'-O-dimethylallyl-substituted nucleotides into oligoribonucleotides to study the effect of these RNA analogues on antisense analysis. Iribarren found that 2'-O-allyl containing oligoribonucleotides are resistant to digestion by either RNA or DNA specific nucleases and slightly more resistant to nucleases with dual RNA/DNA specificity, than 2'-O-methyl oligoribonucleotides. However, Iribarren found that 2'-O-dimethylallyl containing oligoribonucleotides exhibited reduced hybridization to complementary RNA sequences as compared to 2'-O-methyl oligoribonucleotides. Thus, Iribarren suggested that further attempts to prepare alkylated RNA probes, especially those superior to 2'-allyl cytidine containing oligoribonucleotides should be limited to 2'-O-alkyl groups containing less than five carbon atoms.

Certain oligonucleotides containing 2'-O-alkyl substituted nucleotides are promising candidates for use as human pharmaceuticals. Those having long chain alkyl groups (i.e. four or more carbon atoms) are particularly useful. For example, long chain alkyl groups may accomodate functional groups in appropriate orientation with the opposing strand upon strand hybridization. Thus 2'-O-long chain alkyl nucleotides such as 2'-O-long chain alkyl guanosine nucleotides are highly desireable in some cases. For use in large scale therapeutic testing and eventually for human pharmaceutical use, large amounts of these oligonucleotides must be synthesized. The large amounts of oligonucleotides in turn requires large amounts of the 2'-O-alkyl nucleoside phosphoramidites used in synthesizing the oligonucleotides. Consideration must therefore be given to both cost and purity of the starting phosphoramidites used in the synthesis of such oligonucleotides. As a general premise, as the number of synthetic steps increases, the cost of manufacture increases. Further as the number of steps increases, quality control problems escalate. In view of this, it is evident that there is a great need for new and improved procedures for preparing nucleosides and nucleoside phosphoramidites.

OBJECTS OF THE INVENTION

It is an object of this invention to provide methods of synthesis of 2'-O-alkylated nucleosides and nucleoside analogues.

It is an object of this invention to provide methods of synthesis of 2'-O- and 3'-O-alkylated 2,6-diaminopurine riboside compounds.

It is an object of this invention to provide new and improved synthetic methods for the preparation of 2'-O-alkyl nucleoside phosphoramidites.

It is an object of this invention is to provide new and improved syntheses of 2'-O-alkyl guanosine phosphoramidites.

It is an object of this invention is to provide new and improved syntheses of 2'-O-alkyl cytidine phosphoramidites.

It is an object of this invention is to provide new and improved syntheses of 2'-O-alkyl uridine phosphoramidites.

It is an object of this invention is to provide new and improved syntheses of 2,6-diamino-9-(2'-O-alkyl-β-D-ribofuranosyl)purine phosphoramidites.

It is an object of this invention is to provide new and improved oligonucleotide syntheses that utilize the improved phosphoramidite syntheses of the invention.

These and other objects will become apparent to persons of ordinary skill in the art from a review of the present specification and appended claims.

SUMMARY OF THE INVENTION

This invention includes compounds having the structure:

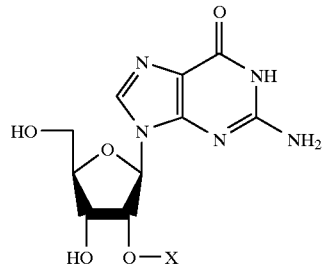

I wherein
  X is $R_1$–$(R_2)_n$;
  $R_1$ is $C_3$–$C_{20}$ alkyl, $C_4$–$C_{20}$ alkenyl or $C_2$–$C_{20}$ alkynyl;
  $R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides; and n is an integer from 0 to about 6.

In other embodiments of the present invention compounds having the structure:

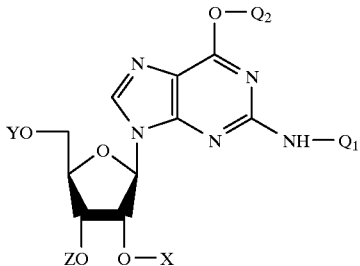

II wherein

X is $R_1-(R_2)_n$;

$R_1$ is $C_3-C_{20}$ alkyl;

$R_2$ is $NH_2$, H-imidazole, N-phthalimido;

Y is a hydroxyl blocking group;

Z is phosphate or an activated phosphate group;

$Q_1$ and $Q_2$ independently are H or a guanosine blocking group; and n is an integer from 0 to about 6, are also provided.

In still other embodiments of the present invention are provided compounds having the structure:

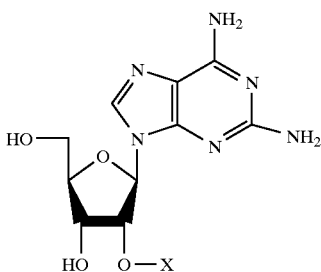

III wherein

X is $R_1-(R_2)_n$;

$R_1$ is $C_3-C_{20}$ alkyl, $C_4-C_{20}$ alkenyl or $C_2-C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, and a group that enhances the pharmacokinetic properties of oligonucleotides; and n is an integer from 0 to about 6.

This invention also includes processes for the facile reparation of 2'-O and 3'-O-monoalkyl or 2',3'-di-O-alkyl substituted guanosine compounds such as compounds of Formulas I, II and III. Except for preparation with diazomethane, heretofore, direct alkylation of guanosine has proven to be refractory. The present invention provides direct 2' and 3'-O-alkylation of 2,6-diamino-9-(-β-D-ribofuranosyl)purine, i.e. 2,6-diaminopurine riboside or 2-aminoadenosine, which can be effected followed by deamination of the 2'-O-alkylated 2,6-diamino purine riboside to the corresponding 2'-O-alkylated guanosine. This alkylation can be practiced, if desired, without the use of blocking groups on either the heterocycle or the sugar moieties of the nucleoside. Further unlike the use of diazomethane, which will only yield the methyl alkylation product, alkylation as practiced in this invention is not limited to just methyl alkylation but is used to yield a plenitude of alkyl substituted guanosine and 2,4-diaminopurine riboside compounds. The necessary compounds used in the invention having the formula R-L wherein R is an alkyl group and L is a leaving group, are either commercially available, are known in the literature or can be prepared by procedures analogous to known literature compounds.

The two step alkylation processes of the invention are further distinguished from the six step procedure of the Sproat et al. investigators. See the above-referenced *Nucleic Acids Research,* 18:41 (1990) and *Nucleic Acids Research,* 19: 733 (1991) publications. In those procedures 2-amino-6-chloropurine riboside must first be blocked at both the 3' and 5' positions, converted to the 2,6-dichloro derivative, blocked at the 6 purine position, derivatized to the 2'-O-methyl or 2'-O-allyl derivative, converted to 2,6-diamino derivative, deblocked about the 3' and 5' positions and finally deaminated to the 2'-O-methyl or 2'-O-allyl guanosine product.

In accordance with the processes of this invention, alkylation is effected directly on 2,6-diamino-9-(β-D-ribofuranosyl)purine with an appropriate compound having the formula R-L, wherein R is an alkyl group and L is a leaving group, in the presence of a base of sufficient strength to effect removal of the proton from the 2' or 3' (or both 2' and 3') hydroxyl of the ribofuranosyl sugar moiety of 2,6-diamino-9-(β-D-ribofuranosyl)purine. Alkylation can be limited to mono alkylation by limiting the amount of either the R-L group or the base to a stoichiometric (or equivalent) amount. Alternately dialkylation (on both the 2' and 3' positions) can be practiced by use of an excess R-L group and base to concurrently alkylate both the 2' and the 3' positions.

While not wishing to be bound by theory, it has been observed that alkylation predominates at the 2' position compared to the 3' position. Generally a ratio of from about 7:3 to about 8:2 of 2' to 3' alkylation products are obtained (as determined by TLC). For both TLC as well as preparative scale chromatography, the 2' product generally has a faster Rf than the 3' product. Advantage can be taken of this Rf difference to separate the 2'-O— and 3'-O— products from each other or from 2'-O—,3'-O— dialkylated products. Thus the 2' and 3' alkylation products can be separated by procedures such as silica gel chromatography if desired.

For alkyl groups that are generally larger than propyl, further advantage can be taken of the rate of deamination of the 2' product verse the 3' product for separation of the 2'-O and 3'-O products. Thus mixtures of 2'-O and 3'-O alkylated 2,6-diamino-9-(β-D-ribofuranosyl)purine are subjected to deamination with adenosine deaminase. The enzymatic deamination of the 2'-O product is more facile than deamination of the 3'-O product. This difference in the rate of deamination allows for separation of the deaminated 2' product, i.e. the 2'-alkylated guanosine, from the slower or non-deaminated 3' product, i.e. the 2,6-diamino-9-(3'-O-alkylated-β-D-ribofuranosyl)purine. Additionally procedures such as crystallization has been utilized to further separate a 2' product from the corresponding 3' product by separating the 2'-O-alkylated diaminopurine riboside product from the corresponding 3'-O-alkylated diaminopurine riboside product.

A preferred base utilized for alkylation is sodium hydride. Other suitable bases may also be utilized, however such bases must have sufficient base strength to remove the proton from the 2' (or 3') hydroxyl moiety of the 2,6-diaminopurine riboside starting material. While not wishing to be bound by theory, generally any base having a $pK_a$ about 10 $pk_a$ units greater than the $pK_a$ of the proton of the 2' hydroxyl moiety of the 2,6-diaminopurine riboside starting material may be used. More specifically, bases having a $pK_b$ greater than the $pK_b$ of sodium hydride may conveniently be selected. Such bases can be selected from compilations of base such as those given in Table 1, page 220 of March, *J. Advanced Organic Chemistry,* Wiley-Interscience, John Wiley & Sons, New York, 1985.

The alkylation reactions of the invention typically are conducted in DMF as the solvent. Other suitable solvents include DMSO, N-methyl pyrolidone and sulfolone.

Preferably, deamination is effected by use of deaminase enzymes. Particularly preferred is adenosine deaminase. Particularly suitable for use is Adenosine Deaminase Type II available from Sigma Chemical Company, St. Louis, Mo. Other deamination reagents may also be employed. The deamination reactions of the invention typically are conducted in a mixture solvent containing an organic solvent and an aqueous buffer. Suitable for use as the organic solvent are DMSO, N-methyl pyrolidone and sulfolone. In preferred embodiments of the present invention deamination is achieved using DMSO as the organic solvent. Suitable for use as the aqueous buffer are buffers having a pH compatible to the pH range of use of the deaminse enzyme. Preferred are phophate buffers such as sodium phosphate and tris buffers.

In order to enrich the 2' product verse 3' product by elimination of any 3' product, a TIPDS (tetraisopropylsiloxane) protecting group is utilized to protect the 3' and 5' hydroxyl moieties of the sugar portions of the 2,6-diaminopurine riboside. In the same manner, exclusive 3' product would be obtainable by use of a base stable, non-migratory 2'-O-protecting group. Such base stable, non-migratory protecting groups include but are not limited to tetrahydropyranyl (THP), 4-methoxytetrahydropyran-4-yl (Mthp), 1-[(2-chloro-4-methyl)phenyl-4-methoxypiperidin-4-yl (Ctmp), triphenylmethyl (trityl), mono-, di- and tri-methoxytrityl and other similar protecting groups.

In accordance with this invention there are also provided improved processes for the preparation of 2'-O-alkylated nucleoside phosphoramidites including 2'-O-alkylated guanosine, cytidine and uridine phosphoramidites.

In accordance with methods of the present invention, preparation of a 2'-O-alkylated guanosine 3'-O-phosphoramidite may comprise the steps of alkylating a 2,6-diamino-9-(ribofuranosyl)purine to form a 2,6-diamino-9-(2'-O-alkylated ribofuranosyl)purine; deaminating said 2,6-diamino-9-(2'-O-alkylated ribofuranosyl)purine to form a 2'-O-alkylated guanosine; blocking the 5'-hydroxyl moiety of said 2'-O-alkylated guanosine; and phosphitylating the 3'-position of said 5'-blocked 2'-O-alkylated guanosine.

Further in accordance with the invention there 2'-O-alkylated cytidine 3'-O-phosphoramidite may be prepared by the steps of alkylating an unblocked cytidine to form a 2'-O-alkylated cytidine; blocking the 5'-hydroxyl moiety of said 2'-O-alkylated cytidine; and phosphitylating the 3'-position of said 5'-blocked 2'-O-alkylated cytidine.

2'-O-alkylated uridine 3'-O-phosphoramidite may be prepared by processes that include the steps of treating a uridine with a dialkyltin oxide to form a 2',3'-O-dialkylstannylene derivative of uridine; alkylating said stannylene derivative of uridine to form a 2'-O-alkylated uridine; blocking the 5'-hydroxyl moiety of said 2'-O-alkylated uridine; and phosphitylating the 3'-position of said 5'-blocked 2'-O-alkylated uridine.

The 3'-O-phosphoramidite of 2'-O-alkyl guanosine and 2,6-diamino-9-(2'-O-alkyl-β-D-ribofuranosyl) purine can be provided in some embodiments of the present invention by reaction of 2-$NH_2$, 5'-OH protected 2'-O-alkyl guanosine or 2-$NH_2$, 6-$NH_2$, and 5'-OH protected 2,6-diamino-9-(2'-O-alkyl-β-D-ribofuranosyl)purine with commercially available reagent known to those skilled in the art such as 2-cyanoethyl N,N-diisopropylaminochlorophosphine.

2'-O-alkyl guanosine and 2'-O-alkyl-2,6-diaminopurine riboside may be phosphitylated at the 3'-OH to provide phosphoramidites by methods known in the art such as by protection of the $NH_2$ moieties (2- or 2- and 6-$NH_2$, respectively) and 5'-OH moiety followed by reaction with cyanoethyl N,N-diisopropyl aminochlorophosphine.

Compounds of the present invention such as are provided herein can be incorporated into oligomers by procedures known to those skilled in the art.

In accordance with methods of the present invention an oligonucleotide that includes at least one 2'-O-alkylated guanosine nucleotide within the oligonucleotide may be prepared by processes comprising the steps of alkylating a 2,6-diamino-9-(ribofuranosyl)purine to form a 2,6-diamino-9-(2'-O-alkylated ribofuranosyl)purine; deaminating said 2,6-diamino-9-(2'-O-alkylated ribofuranosyl)purine to form a 2'-O-alkylated guanosine; blocking the 5'-hydroxyl moiety of said 2'-O-alkylated guanosine; phosphitylating the 3'-position of said 5'-blocked 2'-O-alkylated guanosine to form a 2'-O-alkylated guanosine 3'-O-phosphoramidite; and coupling, utilizing phosphoramidite coupling conditions, said 2'-O-alkylated guanosine 3'-O-phosphoramidite to a 5'-hydroxyl moiety of an oligonucleotide.

Further in accordance with the invention there are provided processes for preparing an oligonucleotide that include at least one 2'-O-alkylated cytidine nucleotide within the sequence of the oligonucleotide, the processes comprise the steps of alkylating a cytidine to provide a 2'-O-alkylated cytidine; blocking the 5'-hydroxyl moiety of said 2'-O-alkylated cytidine; phosphitylating the 3'-position of said 5'-blocked 2'-O-alkylated cytidine to form a 2'-O-alkylated cytidine 3'-O-phosphoramidite; and coupling, utilizing phosphoramidite coupling chemistry, said 2'-O-alkylated cytidine 3'-O-phosphoramidite to a 5'-hydroxyl moiety of an oligonucleotide.

Further in accordance with the invention there are provided processes for preparing an oligonucleotide that include at least one 2'-O-alkylated uridine nucleotide within the sequence of the oligonucleotide, the processes comprise the steps of treating uridine with a dialkyltin oxide to form a 2',3'-O-dialkylstannylene derivative of uridine; alkylating said stannylene derivative to provide a 2'-O-alkylated uridine; blocking the 5'-hydroxyl moiety of said 2'-O-alkylated uridine; phosphitylating the 3'-position of said 5'-blocked 2'-O-alkylated uridine to form a 2'-O-alkylated uridine 3'-O-phosphoramidite; and coupling, utilizing phosphoramidite chemistry, said 2'-O-alkylated uridine 3'-O-phosphoramidite to a 5'-hydroxyl moiety of an oligonucleotide.

Further in accordance with the invention there are provided processes for preparing an oligonucleotide that include at least one 2'-O-alkylated 2,6-diamino-9-(β-D-ribofuranosyl)purine nucleotide within the sequence of the oligonucleotide, the processes comprise the steps of alkylating a 2,6-diamino-9-(β-D-ribofuranosyl)purine to provide a 2'-O-alkylated 2,6-diamino-9-(β-D-ribofuranosyl)purine; blocking the 5'-hydroxyl moiety of said 2'-O-alkylated 2,6-diamino-9-(β-D-ribofuranosyl)purine; phosphitylating the 3'-position of said 5'-blocked 2'-O-alkylated 2,6-diamino-9-(β-D-ribofuranosyl)purine to form a 2'-O-alkylated 2,6-diamino-9-(β-D-ribofuranosyl)purine 3'-O-phosphoramidite; and coupling, utilizing phosphoramidite chemistry, said 2'-O-alkylated 2,6-diamino-9-(β-D-ribofuranosyl)purine 3' -O-phosphoramidite to a 5' -hydroxyl moiety of an oligonucleotide.

Oligomers of the present invention may contain at least one subunit having the structure:

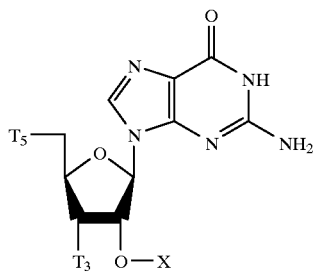

wherein

X is $R_1$–$(R_2)_n$;

$R_1$ is $C_3$–$C_{20}$ alkyl, $C_4$–$C_{20}$ alkenyl $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

$T_3$ and $T_5$ independently are OH or a further nucleotide or nucleoside of said oligonucleotide or oligonucleoside that is joined to said structure; and n is an integer from 0 to about 6.

In still other embodiments of the present invention oligomers of the present invention may contain at least one subunit having the structure:

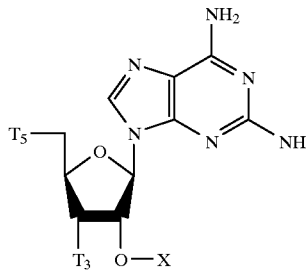

wherein

X is $R_1$–$(R_2)_n$;

$R_1$ is $C_1$–$C_{20}$ alkyl, $C_2$–$C_{20}$ alkenyl $C_2$–$C_{20}$ alkynyl;

$R_2$ is halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, imidazole, N-phthalimido, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

$T_3$ and $T_5$ independently are OH or a further nucleotide or nucleoside of said oligonucleotide or oligonucleoside that is joined to said structure; and n is an integer from 0 to about 6.

Such oligomers or oligonucleotides may be prepared by solid state synthesis or by other means known to those skilled in the art.

In the context of this invention, the term "nucleoside" refers to a sugar and a base that are joined together, normally about an "anomeric" carbon on the sugar. Both α and β sugars are encompassed by the present invention. In preferred embodiments of the present invention the nucleoside sugar is a pentofuranosyl sugar, however, other sugars might also be utilized such as carbocyclic or 4'-deoxy-4'-thio sugar analogs.

In the context of this invention, the term "oligonucleotide" or "oligomer" refers to a polynucleotide formed from naturally occuring bases and furanosyl groups joined by native phosphodiester bonds. Oligonucleotides of the present invention will, of course, comprise at least one 2'-O-alkyl guanosine or derivative thereof. Thus, this term effectively refers to naturally occurring species or synthetic species formed from naturally occurring subunits or their close homologs. The term "oligonucleotide" or "oligomer" may also refer to moieties which have portions similar to naturally occurring oligonucleotides but which have non-naturally occurring portions. Thus, oligonucleotides may have altered sugars, altered base moieties, or altered inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the messenger RNA is located. It is preferred that such substitutions comprise phosphorothioate bonds, phosphotriesters, methyl phosphonate bonds, short chain alkyl or cycloalkyl structures or short chain heteroatomic or heterocyclic structures. Other preferred substitutions are $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ structures where phosphodiester intersugar linkage is replaced by the substitutions. Also preferred are morpholino structures. Summerton, J. E. and Weller, D. D., U.S. Pat. No. 5,034,506 issued Jul. 23, 1991. In other preferred embodiments, such as the protein-nucleic acid (PNA) backbone, the phosphodiester backbone of the oligonucleotide may be replace with a polyamide backbone, the bases being bound directly or indirectly to the aza nitrogen atoms of the polyamide backbone. P. E. Nielsen, et al., *Science* 1991 254 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Suitable bases include, but are not limited to those described in U.S. Pat. 3,687,808. Preferred bases include pyrimidinyl-1 and purinyl-9 moieties such as adenine, guanine, hypoxanthine, uracil, thymine, cytosine, 2-aminoadenine or 5-methylcytosine. Similarly, modifications on the furanosyl portion of the nucleotide subunits, in addition to 2'-O-alkyl modifications of the present invention, may also be effected, as long as the essential tenets of this invention are adhered to. Examples of such modifications are 2'-halogen-substituted nucleotides. Some specific examples of modifications at the 2' position of sugar moieties which are useful in the present invention are OH, SH, $SCH_3$, F, OCN, $O(CH_2)_nNH_2$, Cl, Br, CN, $CF_3$, $OCF_3$, S- or N-alkyl; S- or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide.

Preferably oligonucleotides of the present invention are from about 6 to about 50 nucleotides in length. In still more preferred embodiments of the present invention oligonucleotides are from about 12 to about 20 nucleotides in length.

Further as used in this invention, the term "alkylating" refers to the addition of an alkyl, alkenyl or alkynyl moiety, preferably an alkyl moiety, to the precursors of the nucleosides phosphoramidites of the invention. Alkylation of the 2' position of the nucleoside sugar links the alkylating moiety to the 2' position of the sugar via an ether linkage. Preferred 2'-substituent groups are 2'-poly(ethylene glycol) groups having structure $(O-CH_2-CH_2)_n-O$-alkyl.

Preferred alkyl moieties include un-substituted and substituted straight chain $C_1$–$C_{20}$ alkyl and un-substituted and substituted branch chain $C_1$–$C_{20}$ alkyl. Preferred alkenyl groups include un-substituted and substituted straight chain $C_2$–$C_{20}$ alkenyl, and un-substituted and substituted branch chain $C_2$–$C_{20}$ alkenyl. Preferred alkynyl groups include un-substituted and substituted straight chain $C_2$–$C_{20}$ alkynyl and un-substituted and substituted branch chain $C_2$–$C_{20}$ alkynyl. Thus preferred alkylation groups include but are not limited to $C_1$ to $C_{20}$ straight or branched chain lower alkyl or substituted lower alkyl, $C_2$ to $C_{20}$ straight or branched chain lower alkenyl or substituted lower alkynyl, $C_2$ to $C_{20}$ straight or branched chain lower alkynyl or substituted lower alkynyl.

Alkyl groups of the invention include but are not limited to $C_1$–$C_{20}$ straight and branched chained alkyls such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl, isopropyl, 2-butyl, isobutyl, 2-methylbutyl, isopentyl, 2-methyl-pentyl, 3-methylpentyl, 2-ethylhexyl and 2-propylpentyl. Alkenyl groups include, but are not limited to, unsaturated moieties derived from the above alkyl groups including, but not limited to, vinyl, allyl and crotyl. Alkynyl groups include unsaturated moieties having at least one triple bond that are derived from the above alkyl groups including, but not limited to, ethynyl and propargyl.

Substituent groups for the above include but are not necessarily limited to halogen (Cl, Br, F), hydroxyl (OH), thiol (SH), keto (C=O), carboxyl (COOH), nitrate ($ONO_2$), nitro ($NO_2$), nitroso (NO), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino ($NH_2$), azido ($N_3$), hydrazino ($NHNH_2$), hydroxylamino ($ONH_2$), isocyanato (OCN), sulfoxide (SO), sulfone ($SO_2$), sulfide (S—), disulfide (S—S), silyl, heterocyclic, alicyclic, carbocyclic, intercalators, reporter molecules, conjugates, polyamines, polyamides, polyethylene glycols, polyethers, groups that enhance the pharmacodynamic properties of oligonucleotides, and groups that enhance the pharmacokinetic properties of oligonucleotides. Such compounds include 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups. These substituted groups can be introduced in a blocked or protected form and later de-blocked to the parent substituted compound. For example, use of the phthalimido group as a blocked form of an amino substitution is illustrated below.

Other suitable substituent groups include intercalators, reporter groups, reporter enzymes, and conjugates including cholesterols, phospholipids, biotin, phenanthroline, phenazine, phenanthridine, anthraquinone, acridones, pyrenes, stilbenes, oxazolo-pyridocarbazoles, anthraquinones, phenanthridines, phenazines, azidobenzenes, psoralens, porphyrins, cholic acids, folic acids fluoresceins, rhodamines, coumarins, and dyes; steroids, lipophilic molecules, peptides, protein, vitamins, RNA cleaving complexes, metal chelators, alkylators and cross-linking agents.

One particularly preferred substituent group is $CF_3$. Further particularly preferred substituent groups are phthalimido and imidazole. As noted, use of the phthalimido group allows for introduction of a blocked amino functionality on the alkyl group. Utilizing guanosine analogues prepared in accordance with this invention as intermediates in oligonucleotide synthesis, after oligonucleotide synthesis is complete, the phthalimido group is removed yielding an amino functionality tethered to a guanosine nucleotide within the oligonucleotide sequence. Use of an imidazole moiety as a substituent group on the alkyl functionality introduces the suggested nucleic acid cleaving functionality, imidazole, on a guanosine nucleotide within an oligonucleotide sequence.

Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl, alkynyl and aryl groups including primary and secondary amines and "masked amines" such as phthalimide. Amines are also meant to include polyalkylamino compounds and aminoalkylamines such as aminopropylamine and further heterocyclo-alkylamines such as imidazol-1, 2 or 4-yl-propylamine. RNA cleaving complexes may be, for example, intercalators or groups which bind in the minor groove of RNA. Intercalators are molecules which insert themselves between neighboring bases of an olignoucleotide. Reporter molecules are molecules which may aid in the identification of a molecule, either visually or otherwise. Cross-linking agents effectively join two groups.

Suitable leaving groups of the present invention include halides such as chloride, bromide, and iodide, sulfonates such as tosyl, brosyl, nosyl, mesyl and trifyl and oxonium ions. In preferred embodiments of the present invention the leaving group is a halide. Still other suitable leaving groups are well known to those skilled in the art.

In accordance with methods of the present invention, the alkylation is preferably conducted in the presence of a base, preferably a metal hydride such as sodium hydride. Alkylation of the 2',3'-O-dialkylstannylene derivative of uridine preferably is performed in the presence of a salt such as a metal halide. Cesium flouride and sodium iodide are preferred in some embodiments of the present invention. Additionally, the 5' hydroxyl blocking group is preferably a dimethoxytrityl moiety. The phosphitylating reagent is preferably bis-N, N-diisopropylaminocyanoethylphosphite and the phosphitylating reaction is preferably conducted in the presence of N,N-diisopropylamino-hydrotetrazolide.

In effecting the alkylation of uridine, 2',3'-O-(dibutylstannylene) uridine is alkylated. The dibutylstannylene derivative in turn was prepared in one step from uridine by reaction with dibutyl tin oxide utilizing the procedure of by Wagner, D., Verheyden, J. P. H. and Moffat, J. G., *J. Org. Chem.* 1974, 39:24. As noted by these authors, 2',3'-di-O-(dibutylstannylene) nucleosides are activated towards alkylation. By using the dibutylstannylene derivative alkylation of the sugar hydroxyls was effected without concurrent alkylation of the uracil base. The dibutylstannylene group thus served as a activating group not a blocking group.

For the synthesis of N4-benzoyl-5'-O-(4,4'-dimethoxytriphenylmethyl)-2'-O-methyl cytidine 3'-O-β-cyanoethyl-N,N-diisopropylaminophosphoramidite two methods for the preparation of the intermediate N4-benzoyl-2'-O-methylcytidine are compared. Method A involves blocking of the 3'-5' sites with the TIPS-Cl reagent to allow methylation only on the 2' position. Method B, a preferred method of the invention, uses a direct methylation of cytidine followed by separation of the resulting mixture of 2' and 3' isomers. The overall yields are comparable. In using Method B, the 2'-O-isomer can be crystallized out from the mixture, filtered and the remaining mother liquors taken through the dimethoxytritylation step prior to separation of the 2' and 3' isomers or alternately the totality of the alkylated cytidine can be taken through the dimethoxytritylation step with separation of the 2' isomer only effected after this step.

In effecting the alkylation of guanosine, 2',6 diaminopurine is alkylated, for example, by methods described in Ser. No. 07/967,267 filed Oct. 29, 1992.

The amino moiety of the phosphoramidites of the invention can be selected from various amines presently used for such phosphoramidites. Such amines include both aliphatic and heteroaryl amines as are described in various United States Patents, principally those to M. Caruthers and associates. These include U.S. Pat. Nos. 4,668,777, issued May 26, 1987; 4,458,066, issued Jul. 3, 1984; 4,415,732, issued Nov. 15, 1983; and 4,500,707, issued Feb. 19, 1985, all of which are herein incorporated by reference. One preferred amino group is diisopropylamino.

In addition to the amino moiety of the phosphoramidite, for phosphodiester and phosphorothioate linkages, an additional phosphorous blocking group is used. One preferred blocking group is the cyanoethyl group. Other phosphorous blocking groups include methoxy and 2-(methylsulphonyl) ethyl. Additionally an activating agent is normally used for the phosphoramidite coupling chemistry. One preferred activating agent is N,N-diisopropylaminohydrotetrazolide. Other suitable moieties for these functions are also disclosed in the above noted patents as well as in U.S. Pat. No. 4,725,677, issued Feb. 16, 1988 and Berner, S., Muhlegger, K., and Seliger, H., *Nucleic Acids Research* 1989, 17:853; Dahl, B. H., Nielsen, J. and Dahl, O., *Nucleic Acids Research* 1987, 15: 1729; and Nielson, J. Marugg, J. E., Van Boom, J. H., Honnens, J., Taagaard, M. and Dahl, O., *J. Chem. Research* 1986, 26, all of which are herein incorporated by reference.

For use in phosphorothioate linkage, the Beaucage reagent is described in Beaucage, S. L. and Caruthers, M. H., *Tetrahedron Letters* 1981, 22:1859 as well as in Zon, G. and Stec, J., Phosphorothioate oligonucleotides: *Oligonucleotides and Analogs A Practical Approach;* Eckstein, F. Ed.; IRL Press, Oxford, 1991, which also describes sulfurization by elemental sulfur.

Antisense therapy involves the use of oligonucleotides which are specifically hybridizable to target RNA or DNA. Oligonucleotides of the present invention are preferably specifically hybridizable with a target region. By "specifically hybridizable" herein is meant capable of forming a stable duplex with a target DNA or RNA. Upon binding to, or forming a stable duplex with, the target RNA or DNA, the antisense oligonucleotide can selectively inhibit the genetic expression of these nucleic acids or can induce some other events such as destruction of a targeted RNA or DNA or activation of gene expression. Destruction of targeted RNA can be effected by RNase H activation or by linking strand cleavers to the oligonucleotide. Antisense therapy is known in the art. See for example, PCT/US91/05720 filed Dec. 3, 1991 entitled "Antisense Oligonucleotide Inhibitors of Papillomavirus" and PCT/US91/01327 filed Feb. 25, 1991 entitled "Oligonucleotide Therapies for Modulating the Effects of Herpesvirus".

In some embodiments of the present invention the oligonucleotide portions of compounds of the present invention are at least 60% complementary to a target sequence. In preferred embodiments of the present invention the oligonucleotide portions of compounds of the present invention are at least 80% complementary to a target sequence. 100% complementarity of the oligonucleotide portions of compounds of the present invention to a target sequence is most preferred. In preferred embodiments of the present invention, the oligonucleotide portions may be specifically hybridizable with DNA or RNA from Candida, papilloma virus, Epstein Barr virus, rhinovirus, hepatitis, human immunodeficiency virus, herpes simplex virus, influenza virus and cytomegalovirus.

2'-O-alkyl guanosine containing oligonucleotides and 2,6-diamino purine containing oligonucleotides of the present invention may be used to modulate the production of protein by contacting a selected sequence of RNA or DNA coding for a selected protein with an 2'-O-alkyl guanosine or 2,6-diamino purine containing oligonucleotide of the present invention having a sequence of nucleotide bases specifically hybridizable with said selected sequence of RNA or DNA coding for said protein.

The oligonucleotides of the present invention can be used in diagnostics, therapeutics and as research reagents. For therapeutic use, an animal having a disease characterized by the undesired production of a protein is contacted with an oligonucleotide of the present invention having a sequence of nucleotide bases specifically hybridizable with a selected sequence of RNA or DNA coding for said protein.

EXAMPLES

The following examples illustrate the invention, however, they are not intended as being limiting. In various examples the nomenclature 4,4'-dimethoxytriphenylmethyl and dimethoxytrityl are used interchangeably to reference the DMT blocking group positioned on the 5'-hydroxyl moiety of the various nucleoside and nucleotides of the invention.

NMR spectra were obtained with the following instruments: $^1$H-NMR: Varian Gemini-200 (199.975 MHz), $^{13}$C-NMR: Varian Gemini-200 (50.289 MHz). NMR spectra were recorded using either deuteriochloroform (tetramethylsilane as internal standard) or dimethylsulfoxide-$d_6$ as solvent. The following abbreviations were used to designate the multiplicity of individual signals: s=singlet, d=doublet, t=triplet, q=quartet, ABq=ab quartet, m=multiplet, dd=doublet of doublets, br s=broad singlet. Mass spectra were acquired on a VG 70-SEQ instrument (VG Analytical (Fisons)), using fast atom bombardment ionization (7 kV Xe atoms). Solvent ratios for column chromatography are given as volume/volume. Evaporations of solvents were performed in vacuo (60 torr) at 30° C. unless otherwise specified. Melting points are reported uncorrected.

Example 1

2,6-Diamino-9-(β-D-ribofuranoayl)purine

In accordance with modifications of the procedures described in Robins, M. J., Hanske, F. and Beriner, S. E., *Can. J. Chem.*, 59: 3360 (1981), guanosine hydrate (49 g, Aldrich Chemical Co.), toluene (200 ml), hexamethyldisilazane (160 ml, 4.3 eq) and trifluoromethanesulfonic acid (3.7 ml) were loaded in a stainless steel Parr bomb. The bomb was sealed and heated approximately ⅓ submerged in an oil bath at 170° C. for 5 days. The bomb was cooled in a dry ice acetone bath and opened. The contents were transferred to a 2 liter round bottom flask using methanol (MeOH) and the solvent evaporated on a Buchii evaporator. 1:1 H$_2$O/MeOH (600 ml) was added to the residue and the resulting brown suspension was refluxed 4–5 hr. The resulting suspension was evaporated on the Buchii evaporator to remove the methanol (≈½ volume). Additional H$_2$O (≈300 ml) was added and the mixture was heated, treated with charcoal and filtered through a Celite filter pad. Upon cooling, a crystalline solid formed. The solid was isolated by filtration, washed with H$_2$O and dried under high vacuum at 90° C. to yield the product (43.7 g, 89% yield) as a tan solid. UV and NMR spectra of this compound compared to literature values.

This variation of the procedures of Robins, et al. supra, eliminated the need to utilize liquid ammonia in the reaction mixture since the ammonia molecule is generated in situ from the silazane reagent and the water of hydration of the guanosine hydrate starting material. Further, the use of chlorotrimethylsilane was not necessary nor was it necessary to conduct the reaction under anhydrous conditions, do a preliminary evaporation, or open and re-seal the Parr bomb under a dry nitrogen atmosphere.

Example 2

2,6-Diamino-9-(2'-O-propyl-β-D-ribofuranosyl) purine & 2,6-Diamino-9-(3-O-propyl-β-D-ribofuranosyl)purine Sodium hydride (NaH) (2.1 g) was added to 2,6-diamino-9-(β-D-ribofuranosyl) purine (10.5 g) in dry dimethylformamide (DMF) (150 ml). After stirring for 10 min, iodopropane (6 ml) was added. The solution was stirred for 45 min at room temperature followed by the addition of a further aliquot of NaH (600 mg). The reaction mixture was stirred overnight and then quenched by the addition of ethanol (EtOH) (5 ml). The reaction mixture was evaporated in vacuo, the residue suspended in 10% MeOH/CH$_2$Cl$_2$ and purified by silica gel chromatography (300 g) using 5→10% MeOH/CH$_2$Cl$_2$ as the eluent. The 2',3'-di-O-propyl product eluted first followed by the 2'-O-propyl product and then the 3'-O-propyl product. The 2'-O-propyl product containing fractions were pooled and the solvent stripped to yield a crude foam. The foam was crystallized from H$_2$O (40 ml), washed with cold H$_2$O and dried to yield 2.9 g of the 2'-O-propyl compound. The mother liquor was evaporated, re-chromatographed and crystallized to yield an additional 2.4 g of the 2'-O-propyl compound. The second mother liquor was evaporated to yield 4 g of a mixture of 2' and 3'-O-propyl compounds as an oil. Fractions containing the 3'-O-propyl product as the major product were evaporated and residue crystallized from water. (See Example 17 below for isolation and characterization of the 2',3'-di-O-propyl compound).

2,6-Diamino-9-(2'-O-propyl-β-D-ribofuranosyl) purine $^1$H NMR (DMSO-$\underline{d}_6$) δ 0.76 (t, 3, C$\underline{H}_3$), 1.4 (tq, 2, C$\underline{H}_2$), 3.3 (m, 1, $\underline{H}$-5"+HDO), 3.65–3.45 (m, 3, $\underline{H}$-5', O-C$\underline{H}_2$), 3.9 (m, 1), 4.25 (br m, 1), 4.38 (dd, 1), 5.1 (br d, 1 3'-O$\underline{H}$), 5.45 (br t, 1, 5'-OH), 5.75 (br s, 2, 6-N$\underline{H}_2$), 5.83 (d, 1, $\underline{H}$-1'), 6.77 (br s, 2, 2-N$\underline{H}_2$) and 7.95 (s, 1, $\underline{H}$-8). Anal. Calcd. for C$_{13}$H$_{20}$N$_6$O$_4$·½H$_2$O: C, 46.91; H, 6.2; N,25.25. Found: C, 47.09; H, 6.37; N, 25.33.

2,6-Diamino-9-(3'-O-propyl-β-D-ribofuranosyl) purine $^1$H NMR (DMSO-$\underline{d}_6$) δ 0.75 (t, 3, C$\underline{H}_3$), 1.4 (tq, 2, C$\underline{H}_2$), 3.27–3.5 (ABX 2, O—C$\underline{H}_2$—), 3.5 and 3.6 (ABX, 2, $\underline{H}$-5'), 3.9 (m,1), 4.22 (m, 1), 4.35 (m, 1), 5.1 (br d, 1, 2'-O$\underline{H}$), 5.45 (br t, 1, 5'-O$\underline{H}$), 5.75 (br s, 2, 6-N$\underline{H}_2$), 5.8 (d, 1, $\underline{H}$-1') , 6.8 (br s, 2C$\underline{H}_2$, 2-$\underline{H}_2$) and 7.95 (s, 1, $\underline{H}$-8).

Example 3

2'-O-Propylguanosine

A mixture of 2,6-Diamino-9-(2'-O-propyl-β-D-ribofuranosyl)purine and 2,6-Diamino-9-(3'-O-propyl-β-D-ribofuranosyl)purine (4.6 gm) and adenosine deaminase (200 mg, Sigma Chemicals Type II) were stirred at room temperature overnight in 0.1 M tris buffer (150 ml, pH 7.4), DMSO (100 ml) and 0.1 M sodium phosphate buffer (10 ml). A further aliquot of adenosine deaminase (140 mg) in 0.1 M phosphate buffer (30 ml) and DMSO (20 ml) was added and the reaction stirred an addition 24 hrs. The solvent was evaporated in vacuo and the residue flash chromatographed on silica gel utilizing 5→20% MeOH/CH$_2$Cl$_2$. Product-containing fractions were evaporated in vacuo and the residue crystallized from H$_2$O to yield 2.6 gm of product. m.p. dec >270° C. $^1$H NMR (DMSO-$\underline{d}_6$) δ 0.75 (t, 3, C$\underline{H}_3$), 1.42 (tq, 2, C$\underline{H}_2$), 3.3–3.6 (m, 4, $\underline{H}$-5', O-C$\underline{H}_2$), 3,85 (m, 1), 4.2 (m, 1), 4.23 (m, 1), 5.10 (t, 1, 5'-O$\underline{H}$), 5.13 (d, 1, 3'-O$\underline{H}$), 5.75 (d, 1, $\underline{H}$-1') , 6.45 (br s, 2, N$\underline{H}_2$), 7.95 (s, 1, $\underline{H}$-8) and 10.67 (br s, 1, N$\underline{H}$). Anal. Calcd. for C$_{13}$H$_{19}$N$_5$O$_5$: C, 47.99; H, 5.89; N, 21.53. Found: C, 47.90, H, 5.85; N, 21.44.

Example 4

N2-Isobutyryl-2'-O-propylguanosine

2'-O-Propylguanosine (3.6 gm) in pyridine (50 ml) was cooled in an ice bath and trimethylsilyl chloride (8.4 ml, 6 eq.) was added. The reaction mixture was stirred for 30 min and isobutyryl chloride (5.8 ml, 5 eq.) was added. The solution was stirred for 4 hours during which it was allowed to warm to room temperature. The solution was cooled, $H_2O$ added (10 ml) and the solution was stirred for an additional 30 mins. Concentrated $NH_4OH$ (10 ml) was added and the solution evaporated in vacuo. The residue was purified by silica gel chromatography using 10% $MeOH/CH_2Cl_2$ to elute the product. Product-containing fractions were evaporated to yield 2.5 g of product as a foam. An analytical sample was re-chromatographed on silica and eluted with $CH_2Cl_2 \rightarrow 6\%$ $MeOH/CH_2Cl_2$. $^1H$ NMR (DMSO-$d_6$) δ 0.75 (t, 3, C$\underline{H}_3$), 1.13 [d, 6, CH(C$\underline{H}_3$)$_2$], 1.4 (m, 2, C$\underline{H}_2$) 2.75 [m, 1, C$\underline{H}$(CH$_3$)$_2$], 3.52 (m, 6, OC$\underline{H}_2$), 3.36 and 3.6 (ABX, 2, $\underline{H}$-5'), 3.95 (m, 1), 4.26 (m, 1), 4.33 (m, 1), 5.07 (t, 1, 5'-O $\underline{H}$), 5.18 (d, 1, 3'-O$\underline{H}$), 5.9 (d, 1, $\underline{H}$-1'), 8.25 (s, 1, $\underline{H}$-8), 11.65 (br s, 1, N$\underline{H}$) and 12.1 (br s, 1, N$\underline{H}$). Anal. Calcd. for $C_{17}H_{25}N_5O_6 \cdot \frac{1}{2}H_2O$: C, 50.49; H, 6.48; N, 17.32. Found: C, 50.81; H, 6.62; N, 17.04.

Example 5

N2-Isobutyryl-5'-dimethoxytrityl-2'-O-propylguanosine

N2-Isobutyryl-2'-O-propylguanosine (2.64 g) was co-evaporated with pyridine and then solubilized in pyridine (180 ml). Dimethoxytrityl chloride (2.4 g, 1.1 eq) and dimethylaminopyridine (50 mg) were added with stirring at room temperature. The reaction mixture was stirred overnight and evaporated in vacuo. The residue was partitioned between $CH_2Cl_2/2\times$ dil $Na_2CO_3$. The organic phase was dried (MgSO$_4$) and evaporated. The residue was purified by silica gel chromatography (1:1 EtOAc/Hex→5% MeOH/EtOAc, 1% TEA) to yield 4.1 g of product. $^1H$ NMR (DMSO-$d_6$) δ 0.78 (t, 3, C$\underline{H}_3$), 1.12 [d, 6, CH(C$\underline{H}_3$)$_2$], 1.46 (m, 2, C$\underline{H}_2$), 2.75 [m, 1, C$\underline{H}$(CH3)$_2$], 3.35 and 3.55 (ABX, 2, $\underline{H}$-5'), 3.73 (s, 6, OC$\underline{H}_2$), 4.0 (m, 1), 4.3 (m, 1), 4.4 (m, 1), 5.18 (d, 1, 3'-O$\underline{H}$), 5.93 (d, 1, $\underline{H}$-1'), 6.8, 7.2, 7.36 (m, 13, DMTr), 8.13 (s, 1, $\underline{H}$-8), 11.63 (br s, 1, N$\underline{H}$) and 12.1 (br s, 1, N$\underline{H}$). Anal. Calcd. for $C_{38}H_{42}N_5O_8 \cdot H_2O$: C, 63.83; H, 6.20; N, 9.80. Found: C, 64.22; H, 6.35; N, 9.55.

Example 6

N2-Isobutyryl-5'-dimethoxytrityl-2'-O-propylguanosine 3'-β-cyanoethyl-N,N-diisopropylphosphoramidite A $CH_2Cl_2$ solution of N2-Isobutyryl-5'-dimethoxytrityl-2'-O-propylguanosine (4.1 g), bis-(N,N-diisopropylamino)-2-cyanoethylphosphite (3.7 ml, 2 eq) and N,N-diisopropylammonium tetrazolide (0.5 g, 0.5 eq) was stirred at room temperature overnight. The solution was partitioned against dil. $Na_2CO_3$ and then dil. $Na_2CO_3/NaCl$ and dried over MgSO$_4$. The solvent was evaporated in vacuo and the residue was purified by silica gel chromatography (120 g, 1%TEA in EtOAc) to yield 5.2 g of product as a foam. $^{31}P$ NMR (CDCl$_3$) δ 150.5, 150.8.

Example 7

2,6-Diamino-9-(2'-O-pentyl-β-D-ribofuranosyl) purine & 2,6-Diamino-9-(3'-O-pentyl-β-D-ribofuranosyl)purine 2,6-Diamino-9-(β-D-ribofuranosyl)purine (10 g) was treated with sodium hydride (1.7 g, 1.2 eq) and bromopentane (5.3 ml, 1.2 eq) in DMF (90 ml) as per the procedure of Example 2. Silica gel chromatography yielded three components. The first eluted component (not characterized but believed to be the 2,3-di-(O-pentyl) compound was isolated as an oil (700 mg). The next component isolated as a foam (3.3 g) was crystallized from MeOH to yield 2.8 g of 2,6-diamino-9-(2'-O-pentyl-β-D-ribofuranosyl)purine. The third component isolated as a solid (200 mg) was crystallized from MeOH to yield 80 mg of 2,6-diamino-9-(3'-O-pentyl-β-D-ribofuranosyl)purine. Fractions containing mixtures of the first and second components were evaporated and the residue crystallized from MeOH to yield a further 900 mg of the 2-O-pentyl compound. Further fraction yielded 1.2 g of a mixture of the 2'-O-pentyl and 3'-O-pentyl compounds.

2,6-Diamino-9-(2'-O-pentyl-β-D-ribofuranosyl) purine $^1H$ NMR (DMSO-$d_6$) δ 0.75 (t, 3, C$\underline{H}_3$), 1.16 (m, 4, C$\underline{H}_2$), 1.39 (m, 2, C$\underline{H}_2$), 3.53 (m, 2, C$\underline{H}_2$), 3.3 and 3.6 (ABX, 2, $\underline{H}$-5'), 3.93 (br s, 1), 4.23 (m, 1), 4.38 (m, 1), 5.1 (d, 1 3'-O $\underline{H}$), 5.5 (t, 1, 5'-OH), 5.75 (br s, 2, 6-N$\underline{H}_2$), 5.82 (d, 1, $\underline{H}$-1'), 6.8 (br s, 2, 2-N$\underline{H}_2$) and 7.93 (s, 1, $\underline{H}$-8).

2,6-Diamino-9-(3'-O-pentyl-β-D-ribofuranosyl) purine $^1H$ NMR (DMSO-$d_6$) δ 0.87 (t, 3, C$\underline{H}_3$), 1.3 (m, 4, C$\underline{H}_2$), 1.55 (m, 2, C$\underline{H}_2$), 3.5 (m, 2, O-C$\underline{H}_2$—), 3.6 (m, 2, $\underline{H}$-5'), 3.86 (m, 1), 3.95 (m, 1), 4.6 (m, 1), 5.32 (br d, 1 2'-O$\underline{H}$), 5.46 (br t, 1, 5'-OH), 5.70 (d, 1, $\underline{H}$-1'), 5.75 (br s, 2, 6-N$\underline{H}_2$), 6.76 (br s, 2, 2-N$\underline{H}_2$) and 7.93 (s, 1, $\underline{H}$-8).

Example 8

2'-O-Pentylguanosine 2,6-diamino-9-(2'-O-pentyl-β-D-ribofuranosyl)purine (1.9 g) in 0.1 M sodium phosphate buffer (50 ml, pH 6.0) and DMSO (25 ml) was treated with adenosine deaminase (added in two aliquots—first aliquot 50 mg, second aliquot 80 mg) at 35° C. as per the procedure of Example 3 to yield 1.4 g of product. $^1H$ NMR (DMSO-$d_6$) δ 0.8 (t, 3, C$\underline{H}_3$), 1.16 (m, 4, 2x C$\underline{H}_2$), 1.4 (m, 2, C$\underline{H}_2$), 3.38, 3.6 (m, 4, OC$\underline{H}_2$, H-5'), 3.93 (s, 1, $\underline{H}$-4'), 4.28 (m, 2, $\underline{H}$-2', $\underline{H}$-3'), 5.17 (br, 2, 5', 3'-O$\underline{H}$), 5.8 (d, 1, $\underline{H}$-1'), 6.53 (br s, 2, N$\underline{H}_2$), 8.0 (s, 1, $\underline{H}$-8) and 10.68 (br, 1, N$\underline{H}$).

Example 9

N2-Isobutyryl-2'-O-pentylguanosine

2'-O-pentylguanosine (2.3 g) in pyridine (35 ml) was treated with trimethylsilyl chloride (4.15 ml, 5 eq) and isobutyryl chloride (3.4 ml, 5 eq) as per the procedure of Example 4 to yield the product as a foam (2.3 g). An analytical sample was crystallized from EtOAc/Hex. m.p. 178–180° C. $^1H$ NMR (DMSO-$d_6$) δ 0.75 (t, 3, C$\underline{H}_3$), 1.1 [m, 10, 2x C$\underline{H}_2$, CH(C$\underline{H}_3$)$_2$], 1.4 (m, 2, C$\underline{H}_2$), 2.74 [m, 1, C $\underline{H}$(CH$_3$)$_2$], 3.56 (m, 4, OC$\underline{H}_2$, $\underline{H}$-5'), 3.93 (m, 1, $\underline{H}$-4'), 4.25 (m, 1), 4.34 (m, 1), 5.05 (t, 1, 5'-O$\underline{H}$), 5.17 (d, 1, 3'-O$\underline{H}$), 5.88 (d, 1, $\underline{H}$-1'), 8.27 (s, 1, $\underline{H}$-8), 11.65 (br s, 1, N$\underline{H}$) and 12.05 (br s, 1, N$\underline{H}$). Anal. Calcd. for $C_{19}H_{29}N_5O_6$: C, 53.89; H, 6.90; N, 16.54. Found: 53.75; H, 6.92; N, 16.40

Example 10

N2-Isobutyryl-5'-dimethoxytrityl-2'-O-pentylguanosine

N2-Isobutyryl-2'-O-pentylguanosine (2.3 g) was treated with dimethoxytrityl chloride (1.7 g, 1.1 eq), and dimethylaminopyridine (100 mg as a catalyst) in pyridine (50 ml) as per the procedure of Example 5 to yield the product as a foam (2.9 g). $^1$H NMR (DMSO-$d_6$) δ 0.83 (t, 3, C$\underline{H}_3$), 1.2 [m, 10, 2x C$\underline{H}_2$, CH(C$\underline{H}_3$)$_2$], 1.48 (m, 2, C$\underline{H}_2$), 2.78 [m, 1, C$\underline{H}$(CH$_3$)$_2$], 3.4, 3.6 (m, 4, OC$\underline{H}_2$, $\underline{H}$-5'), 3.75 (s, 6, OC$\underline{H}_3$), 4.07 (m, 1), 4.27 (m, 1), 4.42 (m, 1), 5.2 (br d, 1, 3'-O$\underline{H}$), 5.95 (d, 1, $\underline{H}$-1'), 6.85, 7.25, 7.38 (m, 13, DMTr), 8.15 (s, 1, $\underline{H}$-8), 11.67 (br s, 1, N$\underline{H}$) and 12.1 (br s, 1, N$\underline{H}$). Anal. Calcd. for Anal. Calcd. for C$_{40}$H$_{47}$N$_5$O$_8$·½H$_2$O: C, 65.38; H, 6.58; N, 9.53. Found: C, 65.37; H, 6.59; N, 9.39.

Example 11

N2-Isobutyryl-5'-dimethoxytrityl-2'-O-pentylguanosine 3'-β-cyanoethyl-N,N-diisopropylphosphoramidite N2-Isobutyryl-5'-dimethoxytrityl-2'-O-pentyl-guanosine (1.7 g) was treated with bis-(N,N-diisopropylamino)-2-cyanoethyl-phosphite (1.48 g) and N,N-diisopropylammonium tetrazolide (200 mg) as per the procedure of Example 6 to yield the product (1.4 g) $^{31}$P NMR (CDCl$_3$) δ 150.5, 150.85.

Example 12

2,6-Diamino-9-(2'-O-nonyl-β-D-ribofuranosyl) purine 2,6-Diamino-9-(β-D-ribofuranosyl)purine (50 g, 180 mmol) was treated with sodium hydride (8.8 g, 220 mmol) and bromononane (59 g, 54.4 ml, 285 mmol) in DMF (700 ml) as per the procedure of Example 2 (the diamino compound in DMF was cooled in an ice bath during the addition of NaH) to yield 83 g of crude product. 50 g of crude product was purified by silica gel chromatography. Fraction containing 2'-O-nonyl and 3'-O-nonyl product were combined to give a 77:23 mixture (29 g) of the 2' and 3' product. Pure 2'-O-nonyl product is obtained by chromatography. $^1$H NMR (DMSO-$d_6$) δ 0.95 (t, 3, C$\underline{H}_3$) ; 1.17 [m, 12, O—CH$_2$—CH$_2$—(C$\underline{H}_2$)$_6$]; 1.42 [m, 2, O—CH$_2$C$\underline{H}_2$(CH$_2$)$_6$]; 3.27–3.70 (m, 2, $\underline{H}$-5') ; 3.50–3.70 [m, 2, O—C$\underline{H}_2$(CH$_2$)$_7$]; 3.95 (m, 1, $\underline{H}$-4'), 4.24 (m, 1, $\underline{H}$-3'); 4.40 (m, 1, $\underline{H}$-2'); 5.10 (d, 1, 3'-O$\underline{H}$, J=5 Hz); 5.50 (t, 1, 5'-O$\underline{H}$, J=6 Hz); 5.76 (s, 2, 2-N$\underline{H}_2$); 5.83 (d, 1, $\underline{H}$-1', J=6.0 Hz); 6.81 (s, 2, 6-N$\underline{H}_2$); and 7.96 (s, 1, 8-$\underline{H}$).

Example 13

2'-O-Nonylguanosine

A mixture of 2,6-diamino-9-(2'-O-nonyl-β-D-ribofuranosyl)purine and 2,6-diamino-9-(3'-O-nonyl-β-D-ribofuranosyl)purine (≈80:20 mixture, 29 g) in 0.1 M sodium phosphate buffer (50 ml, pH 7.4), 0.1 M tris buffer (1800 ml, pH 7.4) and DMSO (1080 ml) was treated with adenosine deaminase (1.6 g) as per the procedure of Example 3 to yield 60 g of product as an oil. An analytical product was purified by silica gel chromatography and recrystallized from EtOAc. m.p. 258–259° C. $^1$H NMR (DMSO-$d_6$) δ 0.96 (t, 3, C$\underline{H}_3$, J=7 Hz); 1.17 [m, 12, O—CH$_2$—CH$_2$—(C$\underline{H}_2$)$_6$]; 1.42 [m, 2, O—CH$_2$C$\underline{H}_2$(CH$_2$)$_6$]; 3.27–3.61 (m, 4, $\underline{H}$-5', O—C$\underline{H}_2$(CH$_2$)$_7$]; 3.95 (m, 1, $\underline{H}$-4'), 4.10–4.13 (m, 2, $\underline{H}$-2', $\underline{H}$-3'); 5.13–6.06 (m, 2, 3'-O$\underline{H}$5'-O$\underline{H}$); 5.80 (d, 1, $\underline{H}$-1', J=6.4 Hz); 6.47 (s, 2, 2-N$\underline{H}_2$); 7.98 (s, 1, 8-$\underline{H}$) and 10.64 (s, 1, N$_1$ amide). Anal. Calcd. for C$_{19}$H$_{31}$N$_5$O$_5$: C, 55.73; H, 7.63; N, 17.10. Found: C, 55.67; H, 7.66; N, 17.02.

Example 14

N2-Isobutyryl-2'-O-nonylguanosine

2'-O-nonylguanosine (14.7 g) in pyridine (360 ml) was treated with trimethylsilyl chloride (23.4 ml) and isobutyryl chloride (30.6 ml) as per the procedure of Example 4 to yield crude product (37 g). The crude material was purified by silica gel chromatography (eluted with 90/10 CHCl$_3$/MeOH) to yield 14.6 g of product re-crystallized from EtOAc. m.p. 168–169° C. $^1$H NMR (DMSO-$d_6$) δ 0.85 [t, 3, C$\underline{H}_3$(nonyl)], 1.14 [m, 18, O—C$\underline{H}_2$CH$_2$(C$\underline{H}_2$)$_6$, CH(C$\underline{H}_3$)$_2$], 1.40 [m, 2, O—CH$_2$C$\underline{H}_2$(CH$_2$)$_6$], 2.79 [m, 1, C$\underline{H}$(CH$_3$)$_2$], 3.31–3.63 (m, 4, $\underline{H}$-5', O—C$\underline{H}_2$(CH$_2$)$_7$]; 3.96 (m, 1, $\underline{H}$-4'), 4.27–4.37 (m, 2, $\underline{H}$-2', $\underline{H}$-3'); 5.10 (t, 1, 5'-O$\underline{H}$, J=5 Hz), 5.18 (d, 1, 3'-O$\underline{H}$, J=4 Hz), 5.91 (d, 1, $\underline{H}$-1', J=6.6 Hz), 8.31 (s, 1, 8-$\underline{H}$), 11.73 (s, 1, C$_2$ amide) and 12.11 (s, 1, N$_1$ amide). Anal. Calcd. for C$_{23}$H$_{37}$N$_5$O$_6$: C, 57.60; H, 7.78; N, 14.60. Found: C, 57.63; H, 7.92; N, 14.62.

Example 15

N2-Isobutyryl-5'-dimethoxytrityl-2'-O-nonylguanosine

N2-Isobutyryl-2'-O-nonylguanosine (14.6 g, 30.4 mmol) was treated with dimethoxytrityl chloride (12.1 g, 34 mmol) in pyridine (200 ml) as per the procedure of Example 5 to yield 16 g of purple foam prior to chromatography and 11.5 g after chromatography purification. $^1$H NMR (DMSO-$d_6$) δ 0.84 [t, 3, C$\underline{H}_3$(nonyl), J=7 Hz], 1.16 [m, 18, O—CH$_2$CH$_2$(C$\underline{H}$hd 2)$_6$, CH(C$\underline{H}_3$)$_2$], 1.43 [m, 2, O—CH$_2$C$\underline{H}_2$(CH$_2$)$_6$], 2.77 [m, 1, C$\underline{H}$(CH$_3$)$_2$], 3.18–3.63 (m, 4, $\underline{H}$-5', O—C$\underline{H}_2$(CH$_2$)$_7$]; 3.74 (s, 6, DMTr O-C$\underline{H}_3$) 4.06 (m, 1, $\underline{H}$-4'), 4.27 (m, 1, $\underline{H}$-3'); 4.42 (m, 1, $\underline{H}$-2'); 5.19 (d, 1, 3'-O$\underline{H}$, J=5 Hz), 5.94 (d, 1, $\underline{H}$-1', J=5.7 Hz), 6.83–7.38 (m, 13, DMTr aromatic), 8.14 (s, 1, 8-$\underline{H}$), 11.65 (s, 1, C$_2$ amide) and 12.11 (s, 1, N$_1$ amide). Anal. Calcd. for C$_{44}$H$_{55}$N$_5$O$_8$: C, 67.59; H, 7.27; N, 8.96. Found: C, 67.59; H, 7.11; N, 8.80.

Example 16

N2-Isobutyryl-5'-dimethoxytrityl-2'-O-nonylguanosine 3'-β-cyanoethyl-N,N-diisopropylphosphoramidite N2-Isobutyryl-5'-dimethoxytrityl-2'-O-nonylguanosine (2.1 g) was treated with bis-(N,N-diisopropylamino)-2-cyanoethyl-phosphite (1.5 g) and N,N-diisopropylammonium tetrazolide (0.2 g) as per the procedure of Example 6 to yield the product (2.0 g). $^{31}$P NMR (CDCl$_3$) δ 150.7 and 150.4 (diastereomers).

Example 17

2,6-Diamino-9-(2',3'-di-O-propyl-β-D-ribofuranosyl] purine

The procedure of Example 2 was repeated utilizing 2,6-diamino-9-(β-D-ribofuranosyl)purine (10 g), NaH (3 g) and 1-bromopropane (10 ml) in DMF. After evaporation 1384 of the reaction solvent, the reaction products were purified by silica gel chromatography. The slower moving component yielded 4.3 g of the 2'-O-propyl product as a foam. This foam was crystallized from water to yield 3.6 g of product. The faster moving component isolated as an oil formed crystals upon standing. EtOH was added to the crystals, they were filtered and wash 1×EtOH to yield 1.1 grams of 2',3'-di-O-propyl product. m.p. 165–167° C. $^1$H NMR (DMSO-$d_6$) δ 0.80 and 0.92 (t, 6, C$\underline{H}_3$), 1.6 and 1.45 (m, 4, C$\underline{H}_2$), 3.7–3.45 (br m, 6), 4.07 (m, 2), 4.5 (dd, 1), 5.55 (br t, 1, 5'-O$\underline{H}$), 5.8 (br s, 2, 6-N$\underline{H}_2$), 5.85 (d, 1, $\underline{H}$-1'), 6.84 (br s, 2, 2-N$\underline{H}_2$) and 8.0 (s, 1, $\underline{H}$-8). Anal. Calcd. for C$_{16}$H$_{26}$N$_6$O$_4$: C, 52.45; H, 7.15; N, 22.94. Found: C, 52.18; H, 7.19; N, 22.75.

Example 18

N2,N6-Diisobutyryl-2,6-diamino-9-(2'-O-propyl-β-D-ribofuranosyl)purine

2,6-diamino-9-(2' -O-propyl-β-D-ribofuranosyl)purine (2.0 g) in pyridine (35 ml) was treated with trimethylsilyl chloride (3.9 ml, 5 eq) and isobutyryl chloride (3.2 ml, 5 eq) as per the procedure of Example 4 to yield a foam after silica gel chromatography. The foam was crystallized from EtOAc/Hex to yield 2.2 g of product. m.p. 140–142° C. $^1$H NMR (DMSO-$d_6$) δ 0.77 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.4 (m, 1, $\underline{H}$-5"), 3.58 (m, 3, OC$\underline{H}_2$, $\underline{H}$-5'), 3.95 (m, 1, $\underline{H}$-4'), 4.3 (m, 1), 4.5 (m, 1), 5.02 (t, 1, 5'-O$\underline{H}$), 5.2 (d, 1, 3'-O$\underline{H}$), 6.03 (d, 1, $\underline{H}$-1'), 8.58 (s, 1, $\underline{H}$-8), 10.39 (br s, 1, N$\underline{H}$), and 10.57 (br s, 1, N$\underline{H}$).

Example 19

N2,N6-Diisobutyryl-2,6-diamino-9-(5'-O-dimethoxytrityl-2'-O-propyl-β-D-ribofuranosyl)purine

N2,N6-Diisobutyryl-2,6-diamino-9-(2'-O-propyl-β-D-ribo-furanosyl)purine (1.9 g) was treated with dimethoxytrityl chloride (1.5 g, 1.1 eq), and dimethylaminopyridine (20 mg as a catalyst) in pyridine (50 ml) as per the procedure of Example 5 to yield the product as a foam (2.8 g). $^1$H NMR (DMSO-$d_6$) δ 0.79 (t, 3, C$\underline{H}_3$), 1.07, 1.16 [d, 12, 2×CH(C$\underline{H}_3$)$_2$], 1.5 (m, 2, C$\underline{H}_2$), 2.9, 3.03 [m, 2, 2×C$\underline{H}$(CH$_3$)$_2$], 3.58 (m, 3, OC$\underline{H}_2$, $\underline{H}$-5'), 4.15 (m, 1, $\underline{H}$-4'), 4.4 (m, 1), 4.6 (m, 1), 5.15 (d, 1, 3'-O$\underline{H}$), 6.15 (d, 1, $\underline{H}$-1'), 6.8–7.35 (m, 13, DMTr), 8.5 (s, 1, $\underline{H}$-8), 10.3 (br s, 1, N$\underline{H}$), and 10.57 (br s, 1, N$\underline{H}$).

Example 20

N2,N6-Diisobutyryl-2,6-diamino-9-(5'-O-dimethoxytrityl-2'-O-propyl-β-D-ribofuranosyl)purine 3'-β-cyanoethyl-N,N-diisopropylphoaphoramidite

N2,N6-Diisobutyryl-2,6-diamino-9-(5'-O-dimethoxytrityl-2'-O-propyl-β-D-ribofuranosyl)purine (2.6 g) was treated with bis-(N,N-diisopropylamino)-2-cyanoethylphosphite (1.7 g) and N,N-diisopropylammonium tetrazolide (300 mg) overnight at room temperature. The reaction mixture was partitioned against dil. Na$_2$CO$_3$/CHCl$_2$ and then Na$_2$CO$_3$/NaCl and dried over MgSO$_4$. The organic layer was evaporated to a foam. The foam was dissolved in CH$_2$Cl$_2$ (≈8 ml) and slowly added to Hexanes (500 ml). The solid was filtered and dried to yield the product as a powder (3.1 g). $^{31}$P NMR (CDCl$_3$) δ 150.8 and 151.3.

Example 21

2,6-Diamino-9-[2'-O-[(N-phthalimido)prop-3-yl]-β-D-ribofuranosyl]purine & 2,6-Diamino-9-[3'-O-[(N-phthalimido)prop-3 -yl]-β-D-ribo-furanosyl]purine

2,6-Diamino-9-(β-D-ribofuranosyl)purine (14.2 g) was treated with sodium hydride (3 g, 1.5 eq) and N-(3-bromopropyl) phthalimide (5.3 ml, 1.5 eq) in DMF (20 g) at 70° C. overnight. The reaction mixture was proportioned between H$_2$O and Hexanes (1×) and the aqueous layer then extracted 4×CH$_2$Cl$_2$. The organic layer was dried over MgSO$_4$ and evaporated to a residue. The residue was purified by silica gel chromatography eluted with MeOH/CH$_2$Cl$_2$. The 2'-O-(N-phthalimido)propyl product eluted first followed by mixed fractions and then the 3'-O-(N-phthalimido) product. Evaporations of the fractions gave 3.4 g of the 2'-O-(N-phthalimido)propyl product, 3.0 g of mixed 2' and 3' products and 1.4 g of the 3'-O-(N-phthalimido) propyl product all as foams. The 3'-O-(N-phthalimido) propyl product was crystallized from EtOAc/MeOH to give 270 mg of solid.

2,6-Diamino-9-[2'-O-[(N-phthalimido)prop-3-yl]-β-D-ribofuranosyl]purine

$^1$H NMR (DMSO-$d_6$) δ 1.8 (tq, 2, —C$\underline{H}_2$—), 3.4–3.58 (m, 6, 2x C$\underline{H}_2$, $\underline{H}$-5'), 3.9 (m, 1), 4.26 (m, 1), 4.37 (m, 1), 5.05 (br d, 1, 3'-O$\underline{H}$), 5.4 (br t, 1, 5'-O$\underline{H}$), 5.72 (br s, 2, N$\underline{H}_2$), 5.8 (br d, 1, $\underline{H}$-1'), 6.75 (br s, 2, N$\underline{H}_2$), 7.8 (br s, 4, Ar) and 8.93 (s, 1, $\underline{H}$-8).

2,6-Diamino-9-[3'-O-[(N-phthalimido)prop-3-yl]-β-D-ribofuranosyl]purine m.p. 220–222° C., $^1$H NMR (DMSO-$d_6$) δ 1.85 (tq, 2, –C$\underline{H}$-N), 3.6–3.67 (m, 4, —O—C$\underline{H}_2$, $\underline{H}$-5'), 3.85 (m, 1), 3.92 (m, 1), 4.6 (m, 1), 5.33 (d, 1, 2'-O$\underline{H}$), 5.45 (br t, 1, 5'-O$\underline{H}$), 5.65 (d, 1, $\underline{H}$-1'), 5.73 (br s, 2, N$\underline{H}_2$), 6.75 (br d, 2, N$\underline{H}_2$), 7.8–7.85 (m, 4, Ar) and 7.85 (s, 1, $\underline{H}$-8). Anal. Calcd. for C$_{21}$H$_{23}$N$_7$O$_6$: C, 53.73; H, 4.94; N, 20.88. Found: C, 53.59; H, 4.89; N, 20.63.

Example 22

2'-O-[(N-Phthalimido)prop-3-yl]guanosine

2, 6-diamino-9-[2'-O-[(N-phthalimido)prop-3-yl]-β-D-ribofuranosyl]purine (3.1 g) in 0.1 M sodium phosphate buffer (3 ml, pH 7.4), 0.05 M tris buffer (65 ml, pH 7.4) and DMSO (45 ml) was treated with adenosine deaminase (200 mg) at room temperature for 5 days as per the procedure of Example 3. The product containing fractions from the silica gel chromatography were evaporated and upon concentration formed white crystals. The crystals were filtered and washed with MeOH to yield 1.1 g of product. An analytical sample was recrystallized from MeOH. m.p. 192–194° C. $^1$H NMR (DMSO-$d_6$) δ 1.82 (m, 2, C$\underline{H}_2$), 3.45–3.67 (m, 6, $\underline{H}$-5', OC$\underline{H}_2$, NC$\underline{H}_2$), 3.9 (m, 1), 4.3 (m, 2, $\underline{H}$-2', $\underline{H}$-3'), 5.1 (m, 2, 5' and 3'-O$\underline{H}$), 5.8 (d, 1, $\underline{H}$-1'), 6.5 (br s, 2, N$\underline{H}_2$), 7.83 (s, 4, phthal), 7.98 (s, 1, $\underline{H}$-8) and 10.5 (br s, 1, N$\underline{H}$). Anal. Calcd. for C$_{21}$H$_{22}$N$_6$O$_7$·½H$_2$O: C, 52.61; H, 4.83; N, 17.53. Found: C, 52.52; H, 4.78; N, 17.38.

Example 23

N2-Isobutyryl-2'-O-[(N-phthalimido)prop-3-yl]guanosine

2'-O-[(N-phthalimido)prop-3-yl]guanosine (7.2 g, crude) in pyridine (35 ml) was treated with trimethylsilyl chloride (11.6 ml, 5 eq) and isobutyryl chloride (8 ml, 5 eq) as per the procedure of Example 4 to yield the product as a crude foam (6.5 g). An analytical sample was obtained by crystallization from EtOAc. m.p. 166–168° C. $^1$H NMR (DMSO-$d_6$) δ 1.15 [d, 6, —CH(C$\underline{H}_3$)$_2$], 1.85 (m, 2, C$\underline{H}_2$), 2.8 [m, 1, C$\underline{H}$(CH$_3$)$_2$], 3.45–3.7 (m, 6, H-5', OC$\underline{H}_2$, NC$\underline{H}_2$), 3.95 (m, 1), 4.34 (m, 1), 4.4 (m, 1), 5.12 (t, 1, 5'-O$\underline{H}$), 5.18 (d, 1, 3'-O$\underline{H}$), 5.9 (d, 1, $\underline{H}$-1'), 7.83 (s, 4, phthal), 8.3 (s, 1, $\underline{H}$-8), 11.65 (br s, 1, N$\underline{H}$) and 12.1 (br s, 1, N$\underline{H}$). Anal. Calcd. for C$_{25}$H$_{28}$N$_6$O$_8$·½H$_2$O: C, 54.64; H, 5.32; N, 15.29. Found: C, 54.46; H, 5.39; N, 14.98.

Example 24

N2-Isobutyryl-5'-dimethoxytrityl-2'-O-[(N-phthalimido)prop-3-yl]guanosine

N2-Isobutyryl-2'-O-[(N-phthalimido)prop-3-yl] guanosine (1.2 g) was treated with dimethoxytrityl chloride (820 mg, 1.1 eq), and dimethylaminopyridine (20 mg as a catalyst) in pyridine (50 ml) as per the procedure of Example 5 utilizing 1:1 Hex/EtOAc, then EtOAc then 5%MeOH/EtOAc with 1% TEA as eluent. The product containing fraction were evaporated to yield the product as a foam (1.7 g). $^1$H NMR (DMSO-$\underline{d}_6$) δ 1.1 [d, 6, —CH(C$\underline{H}_3$)$_2$], 1.85 (m, 2, C$\underline{H}_2$), 2.75 [m, 1, C$\underline{H}$(CH$_3$)$_2$], 3.45–3.7 (m, 6, H-5', OC$\underline{H}_2$, NC$\underline{H}_2$), 3.75 (s, 6, OC$\underline{H}_3$), 4.0 (m, 1), 4.32 (m, 1), 4.4 (m, 1), 5.2 (d, 1, 3'-O$\underline{H}$), 5.93 (d, 1, $\underline{H}$-1'), 6.83, 7.2, 7.35 (m, 13, DMTr), 7.78 (s, 4, phthal), 8.15 (s, 1, $\underline{H}$-8), 11.6 (br s, 1, N$\underline{H}$) and 12.05 (br s, 1, N$\underline{H}$). Anal. Calcd. for C$_{46}$H$_{46}$N$_6$O$_{10}$.H$_2$O: C, 64.18; H, 5.62; N, 9.76. Found: C, 64.42; H, 5.78; N, 9.53.

Example 25

N2-Isobutyryl-5'-dimethoxytrityl-2'-O-[(N-phthalimido)prop-3-yl]guanosine 3'-β-cyanoethyl-N,N-diisopropylphosphoramidite N2-Isobutyryl-5'-dimethoxytrityl-2'-O-[(N-phthalimido)prop-3-yl]guanosine (1.6 g) was treated with bis-(N,N-diisopropylamino)-2-cyanoethylphosphite (1.48 g) and N,N-diisopropylammonium tetrazolide (200 mg) as per the procedure of Example 6 to yield the product (2.0 g). $^{31}$P NMR (CDCl$_3$) δ 150.9.

Example 26

N2-Dimethylaminomethylidene-5'-dimethoxytrityl-2'-O-[(N-phthalimido)prop-3-yl]guanosine 2'-O-[(N-phthalimido)prop-3-yl]guanosine (900 mg) in DMF (20 ml) was treated with N,N-dimethylformamide dimethyl acetal (2 ml). The reaction mixture was stirred for 2 hr and evaporated under high vac at 52° C. The residue was co-evaporated 1× with pyridine and taken up in solution in pyridine. Dimethoxytrityl chloride (713 mg, 1.1 eq) and dimethylaminopyridine (20 mg as a catalyst) were added. The reaction mixture was stirred overnight, partitioned between Na$_2$CO$_3$/CH$_2$Cl$_2$, dried over MgSO$_4$ and purified by silica gel chromatography as per the procedure of Example 5 to yield 1.7 g of product as an off white solid. $^1$H NMR (DMSO-$\underline{d}_6$) δ 1.88 (m, 2, C$\underline{H}_2$), 3.1 [d, 6, N=CHN(C$\underline{H}_3$)$_2$], 3.3 (m, 2, $\underline{H}$-5'), 3.67 (m, 4, OC$\underline{H}_2$, NC$_2$), 3.78 (s, 6, 2x OC$\underline{H}_3$), 4.0 (m, 1, $\underline{H}$-4'), 4.35 (m, 2, $\underline{H}$-2', $\underline{H}$-3'), 5.2 (d, 1, 3'-O$\underline{H}$), 5.95 (d, 1, $\underline{H}$-1'), 6.85, 7.25, 7.39 (m, 13, DMTr), 7.85 (s, 4, phthal), 7.95 [s, 1, $\underline{H}$-8), 8.5 (s, 1, N=C$\underline{H}$N(CH$_3$)$_2$] and 11.39 (s, 1, N$\underline{H}_2$). Anal. Calcd. for C$_{45}$H$_{45}$N$_7$O$_9$.½H$_2$O: C, 64.58; H, 5.54; N, 11.71. Found: C, 64.10; H, 5.65; N, 11.47.

Example 27

N2-Dimethylaminomethylidene-5'-dimethoxytrityl-2'-O-[(N-phthalimido)prop-3-yl]guanosine 3'-β-cyanoethyl-N,N-diisopropylphosphoramidite N2-dimethylaminomethylidene-5'-dimethoxytrityl-2'-O-[(N-phthalimido)prop-3-yl]guanosine (1.7 g), bis-(N,N-diisopropylamino)-2-cyanoethylphosphite (1.4 ml) and N,N-diisopropylammonium tetrazolide (170 mg) were stirred overnight at room temperature. The reaction mixture was partitioned between CH$_2$Cl$_2$ and Na$_2$CO$_3$ (2×). The organic phase was dried over MgSO$_4$ and evaporated to an oil. The oil was dissolved in a minimum of CH$_2$Cl$_2$ and added dropwise to ≈900 ml Hexanes to precipitate the product. The solid was isolated and dried to yield 2.1 g of product. $^1$P NMR (CDCl$_3$) δ 150.4, 150.6.

Example 28

2,6-Diamino-9-[2'-O-(N-phthalimido)pent-5-yl]-β-D-ribofuranosyl]purine 2,6-Diamino-(9-β-D-ribofuranosyl)purine (6.7 g) was treated with sodium hydride (1.3 g) and N-(5-bromopentyl) phthalimide (7.8 g, 1.1 eq) in DMF (60 ml) at room temperature for three days. The reaction mixture was proportioned between H$_2$O and CH$_2$Cl$_2$ and extracted 4×CH$_2$Cl$_2$. The combined organic layers were dried over MgSO$_4$ and evaporated. The residue was purified by silica gel chromatography eluted with 5→10% MeOH/CH$_2$Cl$_2$. The 2'-β-(N-phthalimido)pentyl containing fractions were collected and evaporated to a yellow foam to give 2.2 g of product. An analytical sample was crystallized from EtOH. m.p. 173–175° C. $^1$H NMR (DMSO-$\underline{d}_6$) δ 1.2 (m, 2, —C$\underline{H}_2$—), 1.47 (m, 4, 2x C$\underline{H}_2$), 3.55, 3.65 (m, 6, O-C$\underline{H}_2$, $\underline{H}$-5', NC$\underline{H}_2$), 3.95 (m, 1), 4.28 (m, 1), 4.4 (m, 1), 5.13 (d, 1, 3'-O$\underline{H}$), 5.5 (t, 1, 5'-O$\underline{H}$), 5.77 (br s, 2, 6-N$\underline{H}_2$), 5.84 (br d, 1, $\underline{H}$-1'), 6.8 (br s, 2, 2-N$\underline{H}_2$), 7.86 (M, 4, phthal) and 7.95 (s, 1, $\underline{H}$-8). Anal. Calcd. for C$_{23}$H$_{27}$N$_7$O$_6$: C, 55.50; H, 5.47; N, 19.71. Found: C, 55.44; H, 5.51; N, 19.30.

Example 29

2'-O-[(N-Phthalimido)pent-5-yl]guanosine

A mixture of the 2,6-diamino-9-[2' -O-[(N-phthalimido)pent-5-yl]-β-D-ribofuranosyl]purine and 2,6-diamino-9-[3'-O-[(N-phthalimido)pent-5-yl]-β-D-ribofuranosyl]purine isomers (2.2 g) in 0.1 M tris buffer (60 ml, pH 7.4), 0.1 M NaPO$_4$ buffer (2 ml, pH 7.4) and DMSO (40 ml) was treated with adenosine deaminase (60 mg) at room temperature for 5 days as per the procedure of Example 3. The product containing fractions from the silica gel chromatography were evaporated to give the product (1.0 g) as a crude white solid. An analytical sample was prepared by the addition of MeOH to form crystals. m.p. 178–180° C. $^1$H NMR (DMSO-$\underline{d}_6$) δ 1.24 (m, 2, C$\underline{H}_2$), 1.5 (m, 4, 2x C$\underline{H}_2$), 3.5–3.6 (m, 6, $\underline{H}$-5', OC$\underline{H}_2$, NC$\underline{H}_2$), 3.87 (m, 1, $\underline{H}$-4'), 4.25 (m, 2, $\underline{H}$-2', $\underline{H}$-3'), 5.1 (m, 2, 5' and 3'-O$\underline{H}$), 5.78 (d, 1, $\underline{H}$-1'), 6.5 (br s, 2, N$\underline{H}_2$), 7.84 (M, 4, phthal), 7.98 (s, 1, $\underline{H}$-8) and 10.67 (br s, 1, N$\underline{H}$). Anal. Calcd. for C$_{23}$H$_{26}$N$_6$O$_7$.½H$_2$O: C, 54.43; H, 5.36; N, 16.56. Found: C, 54.79; H, 5.24; N, 16.61.

Example 30

N2-Isobutyryl-2'-O-[(N-phthalimido)pent-5-yl]guanosine

2'-O-[(N-phthalimido)pent-5-yl]guanosine (1.6 g, crude) in pyridine (35 ml) was treated with trimethylsilyl chloride (2.0 ml, 5 eq) and isobutyryl chloride (1.68 ml, 5 eq) as per the procedure of Example 4 to yield the product as a foam. This foam was co-evaporated 2× with EtOAc followed by the addition of EtOAc and heating to yield white crystals (950 mg). m.p. 202–204° C. $^1$H NMR (DMSO-$\underline{d}_6$) δ 1.1 [d, 6, —CH(C$\underline{H}_3$)$_2$], 1.17 (m, 2, C$\underline{H}_2$), 1.43 (m, 4, 2x C$\underline{H}_2$), 2.74 [m, 1, C$\underline{H}$(CH$_3$)$_2$], 3.45–3.55 (m, 6, H-5', OC$\underline{H}_2$, NC$\underline{H}_2$), 3.9 (m, 1), 4.25 (m, 1), 4.3 (m, 1), 5.07 (t, 1, 5'-O$\underline{H}$), 5.15 (d, 1, 3'-O$\underline{H}$), 5.87 (d, 1, $\underline{H}$-1'), 7.8 (s, 4, phthal), 8.27 (s, 1, $\underline{H}$-8), 11.67 (br s, 1, N$\underline{H}$) and 12.06 (br s, 1, N$\underline{H}$). Anal. Calcd. for C$_{27}$H$_{32}$N$_6$O$_8$.½H$_2$O: C, 56.14; H, 5.76; N, 14.55. Found: C, 56.45; H, 5.74; N, 14.41.

Example 31

N2-Isobutyryl-5'-dimethoxytrityl-2'-O-[(N-phthalimido)pent-5-yl]guanosine

N2-Isobutyryl-2'-O-[(N-phthalimido)pent-5-yl]guanosine (0.95 g) was treated with dimethoxytrityl chloride (620 mg, 1.1 eq), and dimethylaminopyridine (20 mg as a catalyst) in pyridine (50 ml) as per the procedure of Example 5 utilizing EtOAc 1% TEA and then 5% MeOH EtOAc/CH$_2$Cl$_2$ with 1% TEA as eluent. The product containing fractions were evaporated to yield the product as a foam (1.4 g). $^1$H NMR (DMSO-d$_6$) δ 1.14 [d, 6, —CH(CH$_3$)$_2$], 1.25 (m, 2, CH$_2$), 1.53 (m, 4, 2x CH$_2$), 2.77 [m, 1, CH(CH$_3$)$_2$], 3.3–3.6 (m, 6, H-5', OCH$_2$, NCH$_2$), 3.75 (s, 6, OCH$_3$), 4.07 (m, 1), 4.33 (m, 1), 4.4 (m, 1), 5.18 (d, 1, 3'-OH), 5.94 (d, 1, H-1'), 6.83, 7.2, 7.53 (m, 13, DMTr), 7.8 (s, 4, phthal), 8.15 (s, 1, H-8), 11.6 (br s, 1, NH) and 12.1 (br s, 1, NH). Anal. Calcd. for C$_{48}$H$_{50}$N$_6$O$_{10}$·½H$_2$O: C, 65.52; H, 5.84; N, 9.55. Found: C, 65.55; H, 5.94; N, 9.20.

Example 32

2,6-Diamino-9-[3',5'-O-(tetraisopropyldisiloxane-1, 3-diyl)-β-D-ribofuranosyl]purine To a suspension of 2,6-diamino-9-(β-D-ribofuranosyl)purine (10.5 g) in pyridine (100 ml) was added 1,3-dichlorotetraisopropyldisiloxane (TIPDS, 12.6 g). The reaction was stirred at room temperature for 4 hours and an additional 1.3 g of 1,3-dichlorotetraisopropyldisiloxane was added followed by stirring overnight. The reaction mixture was poured into ice water and the insoluble product (11.6 g) collected by filtration. An analytical sample was recrystallized from EtOAc/Hexanes. m.p. 170–172° C. Anal. Calcd. for C$_{22}$H$_{40}$N$_6$O$_5$Si$_2$·½H$_2$O: C, 49.5; H, 7.74; N, 15.7. Found: 49.57; H, 7.82; N, 15.59.

Example 33

2,6-Diamino-9-[3',5'-O-(tetraisopropyldisiloxane-1, 3-diyl)-2-O-methyl-β-D-ribofuranosyl]purine A mixture of 2,6-Diamino-9-[3,5-O-(tetraisopropyldisiloxane-1,3-diyl)-β-D-ribofuranosyl]purine (8.8 g) in DMF (120 ml) and methyl iodide (3 ml, 3 eq) was cooled in an ice bath and NaH (60% in oil, 1.0 g, 1.5 eq) added. After 20 min the reaction was quenched with MeOH and partitioned between sat. NH$_4$Cl and CH$_2$Cl$_2$. The organic phase was washed with 1×NH$_4$Cl, dried over MgSO$_4$ and evaporated. The residue was crystallized from hot EtOH/H$_2$O to yield the product (8.5 g) as crystals. m.p. 87–89° C. $^1$H NMR (DMSO-d$_6$) δ 1.05 (m, 28, TIPDS), 3.57 (s, 3, OCH$_3$), 3.98 (m, 1, H-4'), 3.92 and 4.07 (ABX, 2, H-5'), 4.13 (d, 1), 4.6 (dd, 1, H-3'), 5.76 (br s, 2, NH$_2$), 5.8 (s, 1, H-1'), 6.77 (br s, 2, NH$_2$) AND 7.77 (s, 1 H-8).

Example 34

2,6-Diamino-9-(2'-O-methyl-β-D-ribofuranosyl) purine

To a solution of 2,6-Diamino-9-[3',5'-O-(tetraisopropyldisiloxane-1,3-diyl)-2'-O-methyl-β-D-ribofuranosyl]purine (8.5 g) in THF (50 ml) was added 1M tetrabutylammonium fluoride in THF (Aldrich, 20 ml). The reaction mixture was stirred for 2 hrs and filtered. The filter cake was washed with 2×EtOAc and air dried to give 4.0 g of crude product. An analytical sample was crystallized from hot MeOH. m.p. 133–135° C. $^1$H NMR (DMSO-d$_6$) δ 3.3 (s, 3, OCH$_3$), 3.58 (m, 2, H-5'), 3.98 (m, 1, H-4'), 4.28 (m, 2, H-2', H-3'), 5.23 (br s, 1, 3'-OH), 5.48 (br t, 1, 5'-OH), 5.77 (br s, 2, NH$_2$), 5.82 (d, 1, H-1'), 6.83 (br s, 2, NH$_2$) and 7.95 (s, 1, H-8). Anal. Calcd. for C$_{11}$H$_{16}$N$_6$O$_4$·½H$_2$O: C, 43.28; H, 5.61; N, 27.52. Found: C, 43.51; H, 5.62; N, 27.26.

Example 35

2'-O-Methylguanosine 2,6-Diamino-9-(2'-O-methyl-β-D-ribofuranosyl)purine (9.5 g) in 0.1M sodium phosphate buffer (200 ml, pH 7.4) and DMSO (25 ml) was treated with adenosine deaminase (Type II Sigma) at RT for 4 days. The resulting suspension was cooled and filtered and the resulting filter cake washed with H$_2$O and dried to a white solid (4.0 g). The solid was recrystallized from hot H$_2$O to yield 2.9 g of product. m.p. 236–238° C. $^1$H NMR (DMSO-d$_6$) δ 3.3 (s, 3, OCH$_3$), 3.53 and 3.6 (ABX, 2, H-5'), 3.87 (m, 1, H-4'), 4.15 (m, 1, H-2'), 4.25 (m, 1, H-3'), 5.13 (t, 1, 5'-OH), 5.23 (d, 1, 3'-OH), 5.8 (d, 1, H-1'), 6.48 (br s, 2, NH$_2$), 7.96 (s, 1, H-8) and 10.68 (br s, 1, NH). Anal. Calcd. for C$_{11}$H$_{15}$N$_5$O$_5$·½H$_2$O: C, 43.14; H, 5.26; N, 22.86. Found: C, 43.59; H, 5.34; N, 23.04.

Example 36

N2-Isobutyryl-2'-O-methylguanosine

2'-O-methylguanosine (3.5 g) in pyridine (100 ml) was treated with trimethylsilyl chloride (9 ml, 6 eq) and isobutyryl chloride (6.2 ml) at RT for 4 hr. The reaction mixture was cooled in an ice bath, H$_2$O (20 ml) was added and stirring continued for an additional 20 min. NH$_4$OH (20 ml) was added and after stirring for 30 min the reaction mixture was evaporated. The residue was triturated with H$_2$O, filtered and the filtrate evaporated and purified by silica gel chromatography as per the procedure of Example 4 to yield the product as an off white solid (1.5 g). $^1$H NMR (DMSO-d$_6$) δ 1.1 [d, 6, CH(CH$_3$)$_2$], 2.77 [m, 1, CH(CH$_3$)$_2$], 3.33–3.6 (m, 5, OCH$_3$, H-5'), 3.93 (m, 1, H-4'), 4.22 (m, 1), 4.3 (m, 1), 5.1 (t, 1, 5'-OH), 5.28 (d, 1, 3'-OH), 5.9 (d, 1, H-1'), 8.28 (s, 1, H-8) and 11.9 (br s, 1, NH).

Example 37

N2-Isobutyryl-5'-dimethoxytrityl-2'-O-methylguanosine

N2-Isobutyryl-2'-O-methylguanosine (1.5 g) was treated with dimethoxytrityl chloride (1.5 g, 1.1 eq), and dimethylaminopyridine (100 mg as a catalyst) in pyridine (50 ml) as per the procedure of Example 5 to yield the product as a foam (2.6 g). $^1$H NMR (DMSO-d$_6$) δ 1.14 (d, 6, CH(CH$_3$)$_2$], 2.75 [m, 1, CH(CH$_3$)$_2$], 3.5 (m, 2, H-5'), 3.74 (s, 6, OCH$_3$), 4.05 (m, 1), 4.33 (m, 1), 5.26 (d, 1, 3'-OH), 5.95 (d, 1, H-1'), 6.83, 7.2, 7.35 (m, 13, DMTr), 8.15 (s, 1, H-8), 11.6 (br s, 1, NH) and 12.1 (br s, 1, NH).

Example 38

N2-Isobutyryl-5'-dimethoxytrityl-2'-O-methylguanosine 3'-β-cyanoethyl-N,N-diisopropylphosphoramidite N2-Isobutyryl-5'-dimethoxytrityl-2'-O-methylguanosine (20 g) was treated with bis-(N,N-diisopropylamino)-2-cyanoethylphosphite (10.8 g) and N,N-diisopropylammonium tetrazolide (1.6 g) as per the procedure of Example 6 to yield the product (15.7 g) $^{31}$P NMR (CDCl$_3$) δ 148.97 and 147.96.

Example 39

N2,N6-Diisobutyryl-2,6-diamino-9-(2'-O-methyl-β-D-ribofuranosyl)purine 2,6-diamino-9-(2'-O-methyl-β-D-ribofuranosyl)purine (700 mg) in pyridine (20 ml) was treated with trimethylsilyl chloride (2.1 ml, 7 eq) and isobutyryl chloride (1.25 ml, 5 eq) as per the procedure of Example 4 to yield the product as a foam (900 mg) after silica gel chromatography.

Example 40

N2,N6-Diisobutyryl-2,6-diamino-9-(5'-O-dimethoxytrityl-2'-O-methyl-β-D-ribofuranosyl) purine N2,N6-Diisobutyryl-2,6-diamino-9-(2'-O-methyl-β-D-ribofuranosyl)purine (900 mg) was treated with dimethoxytrityl chloride (1.0 g) and dimethylaminopyridine (20 mg as a catalyst) in pyridine (30 m) as per the procedure of Example 5 to yield the product as a foam (700 mg). $^1$H NMR (DMSO-$\underline{d}_6$) δ 0.96–1.16 [m, 12, 2x CH(C$\underline{H}_3$)$_2$], 2.9 and 3.05 [M, 2, 2x C$\underline{H}$(CH$_3$)$_2$], 3.18 and 3.37 (ABX, 2, $\underline{H}$-5'), 3.38 (s, 3, OC$\underline{H}_3$), 3.7 (s, 6, OC$\underline{H}_3$), 4.05 (m, 1, $\underline{H}$-4'), 4.44 (m, 2, $\underline{H}$-2',$\underline{H}$-3'), 5.24 (d, 1, 3'-O$\underline{H}$), 6.06 (d, 1, $\underline{H}$-1'), 6.78, 7.2, 7.33 (m, 13, Ar), 8.22 (s, 1, $\underline{H}$-8), 10.3 (br s, 1, N$\underline{H}$) and 10.57 (br s, 1, N$\underline{H}$).

Example 41

N2,N6-Diisobutyryl-2,6-diamino-9-(5'-O-dimethoxytrityl-2'-O-methyl-β-D-ribofuranosyl) purine 3'-βcyanoethyl-N,N-diisopropylphosphoramidite N2,N6-Diisobutyryl-2,6-diamino-9-(5'-O-dimethoxytrityl-2'-O-methyl-β-D-ribofuranosyl)purine (600 mg) was treated with bis-(N,N-diisopropylamino)-2-cyanoethylphosphite (500 μl) and N,N-diisopropylammonium tetrazolide (80 mg) overnight at RT. The reaction mixture was partitioned against dil. Na$_2$CO$_3$/CHCl$_2$ and then Na$_2$CO$_3$/NaCl and dried over MgSO$_4$. The organic layer was evaporated to a foam (500 mg). $^{31}$P NMR (CDCl$_3$) δ 151.1 (doublet).

Example 42

2,6-Diamino-9-(2'-O-octadecyl-β-D-ribofuranosyl) purine 2,6-Diamino-9-(β-D-ribofuranosyl)purine (50 g, 180 mmol) and sodium hydride (7 g) in DMF (1 l) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The product containing fraction were evaporated to yield the product (11 g). $^1$H NMR (DMSO-$\underline{d}_6$) δ 0.84 (t, 3, C$\underline{H}_2$); 1.22 [m, 32, O—CH$_2$—CH$_2$—(C$\underline{H}_2$)$_{16}$—]; 1.86 (m, 2, O—CH$_2$C$\underline{H}_2$—); 3.25 (m, 2, O—C$\underline{H}_2$—); 3.93 (d, 1, 4'$\underline{H}$), 4.25 (m, 1, 3'$\underline{H}$); 4.38 (t, 1, 2'$\underline{H}$); 5.08 (d, 1, 3'-O$\underline{H}$); 5.48 (t, 1, 5'-O$\underline{H}$); 5.75 (s, 2, 6-N$\underline{H}_2$); 5.84 (d, 1, 1'-$\underline{H}$); 6.8 (s, 2, 2-N$\underline{H}_2$); and 7.95 (s, 1, 8-$\underline{H}$).

Example 43

2'-O-octadecylguanosine 2,6-Diamino-9-(2'-O-octadecyl-β-D-ribofuranosyl) purine (10 g) in 0.1 M sodium phosphate buffer (50 ml, pH 7.4), 0.1 M tris buffer (1000 ml, pH 7.4) and DMSO (1000 ml) was treated with adenosine deaminase (1.5 g) as per the procedure of Example 3. At day 3, day 5 and day 7 an additional aliquot (500 mg, 880 mg and 200 mg, respectively) of adenosine deaminase was added. The reaction was stirred for a total of 9 day and after purification by silica gel chromatography yielded the product (2 g). An analytical sample was recrystallized from MeOH $^1$H NMR (DMSO-$\underline{d}_6$) δ 0.84 (t, 3, C$\underline{H}_3$), 1.22 [s, 32, O—CH$_2$—CH$_2$—(C$\underline{H}_2$)$_{16}$], 5.07 (m, 2, 3'-O$\underline{H}$ 5'-O$\underline{H}$); 5.78 (d, 1, 1'-$\underline{H}$); 6.43 (s, 2, N$\underline{H}_2$), 7.97 (s, 1, 8-$\underline{H}$) and 10.64 (s, 1, N$\underline{H}_2$). Anal. Calcd. for C$_{28}$H$_{49}$N$_5$O$_5$: C, 62.80; H, 9.16; N, 12.95. Found: C, 62.54; H, 9.18; N, 12.95.

Example 44

N2-Isobutyryl-2'-O-octadecylguanosine

2'-O-Octadecylguanosine (1.9 g) in pyridine (150 ml) was treated with trimethylsilyl chloride (2 g, 5 eq) and isobutyryl chloride (2 g, 5 eq) as per the procedure of Example 4. The product was purified by silica gel chromatography (eluted with 3% MeOH/EtOAc) to yield 1.2 g of product. $^1$H NMR (DMSO-$\underline{d}_6$) δ 0.85 [t, 3, C$\underline{H}_3$], 1.15 [m, 38, O—CH$_2$CH$_2$(C$\underline{H}_2$)$_{16}$, CH(C$\underline{H}_3$)$_2$], 2.77 [m, 1, C$\underline{H}$(CH$_3$)$_2$], 4.25 (m, 2, 2'$\underline{H}$, 3'$\underline{H}$); 5.08 (t, 1, 5'-O$\underline{H}$), 5.12 (d, 1, 3'-O$\underline{H}$), 5.87 (d, 1, 1'-$\underline{H}$), 8.27 (s, 1, 8-$\underline{H}$), 11.68 (s, 1, N$\underline{H}_2$) and 12.08 (s, 1, N$\underline{H}_2$). Anal. Calcd. for C$_{32}$H$_{55}$N$_5$O$_6$: C, 63.47; H, 9.09; N, 11.57. Found: C, 63.53; H, 9.20; N, 11.52.

Example 45

2,6-Diamino-9-[2'-O-(imidazol-1-yl)butyl-β-D-ribofuranosyl]purine 2,6-Diamino-(9-β-D-ribofuranosyl)purine (5.0 g) in DMF (400 ml) was treated with sodium hydride (0.78 g). After stirring an additional 30 min a further portion of sodium hydride (2.6 g) was added immediately followed by bromobutyl-imidazole (9.9 g) in DMF (25 ml). The reaction mixture was stirred overnight and quenched with H$_2$O. The reaction mixture was filtered through celite and evaporated to yield an oily product. TLC showed a mixture of isomers.

Example 46

2'-O-(Imidazol-1-yl)butylguanosine

A mixture of the 2,6-diamino-9-[2'-O-(imidazol-1-yl) butyl-β-D-ribofuranosyl]purine and 2,6-diamino-9-[3'-O-(imidazol-1-yl)butyl-β-D-ribofuranosyl]purine isomers in 0.1 M tris buffer (pH 7.4), 0.1 M NaSO$_4$ buffer (pH 7.4) and DMSO is treated with adenosine deaminase at RT for 5 days as per the procedure of Example 3. The product containing fractions are purified by silica gel chromatography and the product containing fraction evaporated to give the product.

Example 47

N2-Isobutyryl-2'-O-(imidazol-1-yl)butylguanosine

2'-O-(imidazol-1-yl)butylguanosine in pyridine will be treated with trimethylsilyl chloride (5 eq) and isobutyryl chloride (5 eq) as per the procedure of Example 4 to yield the product.

Example 48

N2-Isobutyryl-5'-dimethoxytrityl-2'-O-(imidazol-1-yl)butylguanosine

N2-Isobutyryl-2'-O-(imidazol-1-yl)butylguanosine will be treated with dimethoxytrityl chloride (1.1 eq), and dimethylaminopyridine (as a catalyst) in pyridine as per the procedure of Example 5. After chromatography purification, the product containing fractions will be evaporated to yield the product).

Example 49

2',3'-O-Dibutylstannylene uridine

Utilizing the protocol of Wagner, et al., *J. Org. Chem.* 1974, 39, 24, uridine (45 g, 0.184 mol) was refluxed with di-n-butyltinoxide (45 g, 0.181 mol) in 1.4 l of anhydrous methanol for 4 hrs. The solvent was filtered and the resultant 2',3'-O-dibutylstannylene-uridine was dried under vacuum at 100° C. for 4 hrs to yield 81 g (93%).

Example 50

2'-O-[Pentyl-ω-(N-phthalimido)]uridine

2',3'-O-Dibutyl stannylene-uridine was dried over P$_2$O$_5$ under vacuum for 12 hrs. To a solution of this compound (20 g, 42.1 mmols) in 500 ml of anhydrous DMF were added 25 g (84.2 mmols) of N(5-bromopentyl)phthalimide (Trans World Chemicals, Rockville, Md.) and 12.75 g (85 mmols) of cesium fluoride (CsF). The mixture was stirred at room temperature for 72 hrs. The reaction mixture was evaporated then co-evaporated once with toluene and the residue was partitioned between EtOAc and water (400 ml each). The EtOAc layer was concentrated and applied to a silica column (700 g). Elution with $CH_2Cl_2$—$CH_3OH$ (20:1, v/v) gave fractions containing a mixture of the 2'- and 3'-isomers of O-pentyl-ω-N-phthalimido uridine, in 50% yield.

Example 51

5'-O-Dimethoxytrityl-2'-O-[pentyl-ω-(N-phthalimido)]uridine

The isomeric mixture of 2'-O-[pentyl-ω-(N-phthalimido)] uridine was allowed to react with DMT chloride in dry pyridine at room temperature for 6 hrs. $CH_3OH$ was used to quench excess DMT-Cl and the residue was partitioned between $CH_2Cl_2$ containing 0.5% $Et_3N$ and water. The organic layer was dried ($MgSO_4$) and the residue was applied to a silica column. The column was eluted with $CH_2Cl_2$:$CH_3OH$ (20:1, v/v) to separate the 2' and 3' isomers of the product.

Example 52

5'-O-Dimethoxytrityl-2'-O-[pentyl-ω-(N-phthalimido)]uridine-3'-O-(β-cyanoethyl N,N-diisopropylphosphoramidite)

5'-O-Dimethoxytrityl-2'-O-[pentyl-ω-(N-phthalimido)] uridine was placed in a dry round bottom flask containing a teflon stir-bar. The flask was purged with argon. Anhydrous methylene chloride was added to the flask in an amount sufficient to dissolve the nucleoside. Previously vacuum dried N,N-diisopropylaminohydrotetrazolide (600 mg, 0.014 mol) was added under argon. Bis-N,N-diisopropylamino-cyanoethylphosphite was added via syringe. The reaction was stirred under argon at 25° C. for 16 h. Upon completion of the reaction, the reaction was transferred to a separatory funnel. The reaction flask was rinsed with methylene chloride (2×50 mL). The combined organic layer was washed 2× with sat'd aq. sodium bicarbonate. The organic layer was dried over magnesium sulfate, evaporated and taken up in toluene containing 1% triethylamine. The resulting phosphoramidite was purified by silica gel flash chromatography and eluted with 3:1→1:1 Hexanes/ethyl acetate containing 1% triethylamine. Selected fractions were combined, concentrated under reduced pressure and dried to yield the product as a white foam. $^{31}$P-NMR ($CDCl_3$, $H_3PO_4$ std.) showed the correct diastereomers

Example 53

2'-O-Pentyluridine

Utilizing the procedures of Examples 50 and 51, 2',3'-O-dibutylstannylene uridine (19.1 g) was treated with bromopentane (7 ml, 1.3 eq.) and sodium iodide (4.5 g) in DMF (90 ml). Purification on a silica gel column utilizing MeOH/$CH_2Cl_2$ 5%→10% yielded the a mixture of 2' and 3' isomers of the product as a dark oil (9.8 g).

Example 54

5'-O-Dimethoxytrityl-2'-O-pentyluridine

The mixture of 2'-O-pentyluridine and 3'-O-pentyluridine (9.8 g) was reacted with dimethoxytrityl chloride (10.5 g) as per the procedure of Example 51. The crude product was purified on a silica gel column (1000 g). Elution with Hex.-EtOAc (3:1→1:1) gave 5.5 g of the 2'-O-pentyl isomer and 3 g of the 3'-O-pentyl isomer. Anal. Calcd. for $C_{35}H_{37}N_2O_8$.½$H_2O$: C, 67.51; H, 6.55; N, 4.5. Found: C, 67.48; H, 6.55; N, 4.5.

Example 55

5'-O-Dimethoxytrityl-2'-O-pentyluridine-3-O-(β-cyanoethyl N,N-diisopropylphosphoramidite)

The protected 5'- O-dimethoxytrityl-2'-O-pentyluridine (4.6 g. 0.007 mol) was placed in a dry round bottom flask containing a teflon stir-bar. The flask was purged with argon. Anhydrous methylene chloride was added to the flask in an amount sufficient to dissolve the nucleoside. Previously vacuum dried N,N-diisopropylaminohydrotetrazolide (600 mg, 0.014 mol) was added under argon. Bis-N,N-diisopropylaminocyanoethylphosphite (4.5 g, 4.7 ml, 2 eq.) was added with stirring via syringe. The reaction was stirred under argon at 25° C. for 16 h. After verifying the completion of the reaction by TLC, the reaction was transferred to a separatory funnel and the reaction flask was rinsed with methylene chloride (2×50 mL). The combined organic layer was washed 2× with sat'd aq. sodium bicarbonate. The organic layer was dried over magnesium sulfate, evaporated and taken up in toluene containing 1% triethylamine. The resulting phosphoramidite was purified by silica gel flash chromatography (300 g) and eluted with Hexanes/ethyl acetate (3:1→1:1 containing 1% triethylamine). Selected fractions were combined, concentrated under reduced pressure and dried to yield 2.67 g of product as a white foam. $^{31}$P-NMR ($CDCl_3$, $H_3PO_4$ std.) showed the correct diastereomers

Example 56

2'-O-Methyluridine

As per the procedure of Example 49, uridine (8.5 g) was treated with dibutyl tin oxide (8.2 g, 1 eq). The resulting 2',3'-O-dibutylstannylene uridine was treated with iodomethane (16 ml) at 42° C. as per Example 50 to give a mixture of the 2' and 3' alkylated products (3.5 g) as a foam.

Example 57

5'-O-(4,4'-Dimethoxytriphenylmethyl)-2'-O-methyluridine

2'-O-Methyluridine (8.0 g, 0.031 mol) was evaporated under reduced pressure with pyridine (100 mL) to an oil. To the residue was added 4,4'-dimethoxytriphenylmethyl chloride (DMT-Cl, 11.5 g, 0.34 mol) and pyridine (100 mL). The mixture was stirred at 25° C. for 1.5 h and then quenched by the addition 10 of methanol (10 mL) for 30 min. The mixture was concentrated under reduced pressure and the residue was chromatographed on silica gel (250 g), Elution with hexanes-ethyl acetate-triethylamine (80:20:1) and then ethyl acetate-triethylamine (99:1). The appropriate fractions were combined, evaporated under reduced pressure and dried at 25° C./0.2 mmHg for 1 h to provide 17.4 g (100%) of tan foam; TLC purity 98% (Rf 0.23, hexanes-ethyl acetate 4:1); PMR (DMSO) d 11.4 (H-$N^3$), 7.78 (H-6), 7.6–6.8 (Bz), 5.8 (H-1'), 5.3 (H-5'), 5.25 (HO-3'), 3.7 ($CH_3O$-Bz), 3.4, ($CH_3O$-2').

Example 58

5'-O-(4,4'-dimethoxytriphenylmethyl)-2'-O-methyluridine-3'-O-(β-cyanoethyl N,N-diisopropylphosphoramidite)

The product was prepared as per Example 54 from the intermediate 5'-O-(4,4'-dimethoxytriphenylmethyl)-2'-O- methyluridine. Ethyl acetate-hexanes-triethylamine (59:40:1) was used as the chromatography eluent to give the product as a solid foam in 60% yield. TLC homogenous diastereomers, Rf 0.58; 0.44 [ethyl acetate-hexanes-triethylamine 59:40:1)]. $^{31}$P-NMR (CDCl$_3$, H$_3$PO$_4$ std.) d 148.11; 148.61 (diastereomers).

Example 59

2'-O-Propyluridine

As per the procedure of Example 49, uridine (10 g) was treated with dibutyl tin oxide (10.2 g, 1 eq). The resulting 2',3'-O-dibutylstannylene uridine was treated with iodopropane (8 ml, 2 eq.) at 110° C. as per Example 50 to give a mixture of the 2' and 3' isomers (5.5 g) as a foam.

Example 60

5'-O-(4,4'-Dimethoxytriphenylmethyl)-2'-O-propyluridine

The mixture of 2'-O-propyluridine and 3'-O-propyluridine (3.6 g) was reacted with dimethoxytrityl chloride (4.2 g, 1.0 eq.) as per Example 51. The residue was chromatographed on silica gel eluted with Hex/EtOAc (1:1 with 1% triethylamine). The appropriate fractions were combined, evaporated under reduced pressure and dried to provide 4.2 g of a white foam. Anal. Calcd. for C$_{33}$H$_{36}$N$_2$O$_8$.½H$_2$O: C, 67.33; H, 6.16; N, 4.76. Found: C, 67.15; H, 6.24; N, 4.44.

Example 61

5'-O-(4,4'-dimethoxytriphonylmethyl)-2'-O-propyluridine-3'-O-(β-cyanoethyl N,N-diisopropylphosphoramidite)

The product was prepared as per Example 54 from the intermediate 5'-O-(4,4'-dimethoxytrityl)-2'-O-propyluridine (470 mg) to yield the product as a foam (477 mg).

Example 62

2'-O-Nonyluridine

As per the procedure of Example 49, uridine (22.5 g) was treated with dibutyl tin oxide (22.5 g, 1 eq). The resulting 2',3'-O-dibutylstannyleneuridine was treated with iodononane (11 ml, 1.3 eq.) at 130–140° C. as per Example 50 to give the 2' and 3' isomers (11.2 g) as an oil.

Example 63

5'-O-(4,4'-Dimethoxytriphenylmethyl)-2'-O-nonyluridine

The mixture of 2'-O-nonyluridine and 3'-O-nonyluridine (11.2 g) was reacted with dimethoxytrityl chloride (10.5 g) as per Example 51. The residue was chromatographed on silica gel eluted with Hex/EtOAc (3:1→1:1 with 1% triethylamine). The appropriate fractions were combined, evaporated under reduced pressure and dried to provide 5.2 g of a foam. An analytical sample was rechromatographed using toluene/EtOAc (3:1 with 1% triethylamine) Anal. Calcd. for C$_{39}$H$_{48}$N$_2$O$_8$: C, 69.62; H,. 7.19; N, 4.16. Found: C, 69.66; H, 7.18; N, 4.06.

Example 64

5'-O-(4,4'-dimethoxytriphenylmethyl)-2'-O-nonyluridine-3'-O-(β-cyanoethyl N,N-diisopropylphosphoramidite)

The product was prepared as per Example 54 from the intermediate 5'-O-(4,4'-dimethoxytrityl)-2'-O-nonyluridine (3.1 g) to yield the product as a foam (2.49 g).

Example 65

2'-O-Hexenyluridine

As per the procedure of Example 49, uridine (10.5 g) was treated with dibutyl tin oxide (10.5 g, 1 eq). The resulting 2',3'-O-dibutylstannyleneuridine was treated with 6-bromohexene (3.5 ml, 1.2 eq.) and sodium iodide (3.3 g, 1.o eq.) at 115° C. as per Example 50 to give the 2' and 3' isomers (3.3 g) as a foam.

Example 66

5'-O-(4,4'-Dimethoxytriphenylmethyl)-2'-O-hexenyluridine

The mixture of 2'-O-hexenyluridine and 3'-O-hexenyluridine (3.1 g) was reacted with dimethoxytrityl chloride (3.5 g, 1.1 eq.) as per Example 51. The residue was chromatographed on silica gel eluted with Hex/EtOAc (3:1→1:1 with 1% triethylamine). The appropriate fractions were combined, evaporated under reduced pressure and dried to provide 2.3 g of a white foam. Anal. Calcd. for C$_{36}$H$_{40}$N$_2$O$_8$.½H$_2$O: C, 67.80; H, 6.48; N, 4.39. Found: C, 68.77; H, 6.41; N, 4.45.

Example 67

5'-O-(4,4'-Dimethoxytriphenylmethyl)-2'-O-hexenyluridine-3'-O-(β-cyanoethyl N,N-diisopropylphosphoramidite)

The product is prepared as per Example 54 from the intermediate 5'-O-(4,4'-dimethoxytrityl)-2'-O-hexenyluridine.

Example 68

5'-O-Dimethoxytrityl-2'-O-[hexyl-ω-(N-phthalimido)]uridine-3'-O-(β-cyanoethyl N,N-diisopropylphosphoramidite)

In a like manner as per Examples 50 through 52, using N-(6-bromohexyl) phthalimide, an N-phthalimide substituted hexyl group was introduced at the 2'-position of uridine followed by dimethoxytritylation and phosphitylation to give the title nucleotide.

Example 69

5'-O-Dimethoxytrityl-2-O-[decyl-ω-(N-phthalimido)]uridine-3-O-(β-cyanoethyl N,N-diisopropylphosphoramidite)

In a like manner as per Examples 50 through 52, using N-(10-bromodecyl)phthalimide, an N-phthalimide substituted decyl group was introduced at the 2'-position of uridine followed by dimethoxytritylation and phosphitylation to give the title nucleotide.

Example 70

N4-Benzoyl-2'-O-methylcytidine, Method A

Step 1. 3',5'-O-[(1,1,3,3-Tetraisopropyl)-1,3-disiloxanediyl]cytidine

With stirring, cytidine (40 g, 0.165 mol) and 1,3-dichloro-1,1,3,3-tetraisopropyldisiloxane (TIPS-Cl, 50 g, 0.159 mol) were added to dry pyridine (250 mL). After stirring for 16 h at 25° C., the reaction was concentrated under reduced pressure to an oil. The oil was dissolved in methylene chloride (800 mL) and washed with sat'd sodium bicarbonate (2×300 mL). The organic layer was passed through a silica gel (200 g) scrub column. The product was recovered by elution with methylene chloride-methanol (97:3). The appropriate fractions were combined, evaporated under reduced pressure and dried at 25° C./0.2 mmHg for 1 h to give 59.3 g (77%) of oil. TLC purity 95% (Rf 0.59, ethyl acetate-methanol 9:1). The product may be crystallized from ethyl acetate as white crystals, mp 242–244° C. 41 PMR (DMSO) d 7.7 ( H-6), 5.68 (H-5), 5.61 (HO-2'), 5.55 (H-1').

Step 2. N4-Benzoyl-3'-5'-O-[(1,1,3,3)tetraisopropyl-1,3-disiloxanediyl]cytidine

Benzoyl chloride (18.5 g, 0.13 mol) was added over 30 min to a stirred solution of 3',5'-O-[(1,1,3,3-tetraisopropyl)-1,3-disiloxanediyl]cytidine (58 g, 0.12 mol) and triethylamine (15.6 g, 0.16 mol) in dimethylacetamide (400 mL) at 5° C. The mixture was allowed to warm to 25° C. for 16 h and then poured onto ice water (3.5 L) with stirring. The resulting solid was collected, washed with ice water (3×500 mL) and dried at 45° C./0.2 mmHg for 5 h to provide 77 g (100%) of solid. TLC purity ca. 90% (Rf 0.63, chloroform-methanol 9:1); PMR (CDCL$_3$) d 8.32 (H-6); mp 100–101° C.

Step 3. N4-Benzoyl-2'-O-methyl-3',5'-O-[(1,1,3,3)tetraisopropyl-1,3-disiloxanediyl]cytidine A mixture of N4-benzoyl-3'-5'-O-[(1,1,3,3)tetraisopropyl-1,3-disiloxanediyl]cytidine (166 g, 0.25 mol, 90% purity), silver oxide (150 g, 0.65 mol) and toluene (300 mL) was evaporated under reduced pressure. More toluene (500 mL) was added and an additional amount (100 mL) was evaporated. Under a nitrogen atmosphere, methyl iodide was added in one portion and the reaction was stirred at 40° C. for 16 h. The silver salts were collected and washed with ethyl acetate (3×150 mL). The combined filtrate was concentrated under reduced pressure. The residue was dissolved in a minimum of methylene chloride, applied to a silica gel column (1 kg) and eluted with hexanes-ethyl acetate (3:2→1:1). The appropriate fractions were combined, concentrated under reduced pressure and dried at 45° C./0.2 mmHg for 1 h to yield 111 g (66%) of oil; TLC purity ca. 90% (Rf 0.59, hexanes-ethyl acetate 3:2). PMR (CDCl$_3$) d 8.8 (br s, 1 , H-N$^4$), 8.40 (d, 1, H-6), 8.0–7.4 (m, 6, H-5 and Bz), 5.86 (s, 1, H-1'), 3.74 (s, 3, CH$_3$O-2').

Step 4. N4-Benzoyl-2'-O-methylcytidine

A solution of N4-benzoyl-2'-O-methyl-3',5'-O-[(1,1,3,3) tetraisopropyl-1,3-disiloxanediyl]cytidine (111 g, 0.18 mol) in methanol (160 mL) and tetrahydrofuran (640 mL) was treated with tetrabutylammonium fluoride solution (368 mL, 1 M in tetrahydrofuran). The reaction was stirred at 25° C. for 16 h. The pH was adjusted to 7 with Amberlite IRC-50 resin. The mixture was filtered and the resin was washed with hot methanol (2×200 mL). The combined filtrate was concentrated under reduced pressure, absorbed on silica gel (175 g) and chromatographed on silica gel (500 g, ethyl acetate-methanol 19:1→4:1). Selected fractions were combined, concentrated under reduced pressure and dried at 40° C./0.2 mmHg for 2 h to yield 28 g (42.4%, 21.5% from cytidine) of solid; TLC homogenous (Rf 0.37, ethyl acetate). mp 178–180° C. (recryst. from ethanol); PMR (CDCl$_3$) d 11.22 (br s, 1, H-N$^4$), 8.55 (d, 1, H-6), 8.1–7.2 (m, 6, H-5 and Bz), 5.89 (d, 1, H-1'), 5.2 (m, 2, HO-3',5'), 3.48 (s, 3, CH$_3$O-2').

Example 71

N4-Benzoyl-2'-O-methylcytidine, Method B

Step 1. 2'-O-methylcytidine

Cytidine (100 g, 0.41 mol) was dissolved in warm dimethylformamide (65° C., 1125 mL). The solution was cooled with stirring to 0° C. A slow, steady stream of nitrogen gas was delivered throughout the reaction. Sodium hydride (60% in oil, washed thrice with hexanes, 18 g, 0.45 mol) was added and the mixture was stirred at 0° C. for 45 min. A solution of methyl iodide (92.25 g, 40.5 mL, 0.65 mol) in dimethylformamide (400 mL) was added in portions over 4 h at 0° C. The mixture was stirred for 7 h at 25° C. and then filtered. The filtrate was concentrated to dryness under reduced pressure followed by co-evaporation with methanol (2×200 mL). The residue was dissolved in methanol (350 mL). The solution was adsorbed on silica gel (175 g) and evaporated to dryness. The mixture was slurried in dichloromethane (500 mL) and applied on top of a silica gel column (1 kg). The column was eluted with a gradient of dichloromethane-methanol (10:1→2:1). The less polar 21,3'-dimethyl side product was removed and the co-eluting 2' and 3'-O-methyl product containing fractions were combined and evaporated under reduced pressure to a syrup. The syrup was dissolved in a minimum of hot ethanol (ca. 150 mL) and allowed to cool to 25° C. The resulting precipitate (2' less soluble) was collected, washed with ethanol (2×25 ml) and dried to give 15.2 g of pure 2'-O-methylcytidine; mp 252–254° C. mp 252–254° C.); TLC homogenous (Rf 0.50, dichloromethane-methanol 3:1, (Rf of 3' isomer 0.50 and the dimethyl product 0.80). The filtrate was evaporated to give 18 g of a mixture of isomers and sodium iodide.

Step 2. N4-Benzoyl-2'-O-methylcytidine

The pure 2'-O-methylcytidine (15.2 g, 0.060 mol) was dissolved in a solution of benzoic anhydride (14.7 g, 0.12 mol) in dimethylformamide (200 mL). The solution was stirred at 25° C. for 48 h and then evaporated to dryness under reduced pressure. The residue was triturated with methanol (2×200 mL), collected and then triturated with warm ether (300 mL) for 10 min. The solid was collected and triturated with hot 2-propanol (50 mL) and allowed to stand at 4° C. for 16 h. The solid was collected and dried to give 17 g of product. The crude filtrate residue (18 g) of 2'-O-methylcytidine was treated with benzoic anhydride (17.3 g, 0.076 mol) in dimethylformamide (250 mL) as above and triturated in a similar fashion to give an additional 6.7 g of pure product for a total yield of 23.7 g (16% from cytidine) of solid; TLC homogenous (Rf 0.25, chloroform-methanol 5:1, co-spots with material made utilizing Method A)

Example 72

N4-Benzoyl-5'-O-(4,4'-dimethoxytriphenylmethyl)-2'-O-methyl-cytidine

N4-Benzoyl-2'-O-methylcytidine, (28 g, 0.077 mol) was evaporated under reduced pressure to an oil with pyridine (400 mL). To the residue was added 4,4'-dimethoxytriphenylmethyl chloride (DMT-Cl, 28.8 g, 0.085 mol) and pyridine (400 mL). The mixture was stirred at 25° C. for 2 h and then quenched by the addition of methanol (10 mL) for 30 min. The mixture was concentrated under reduced pressure and the residue was chromatographed on silica gel (500 g, hexanes-ethyl acetate-triethylamine 60:40:1 and then ethyl acetate-triethylamine 99:1). The appropriate fractions were combined, evaporated under reduced pressure and dried at 40° C./0.2 mmHg for 2 h to give 26 g (74%) of foam; TLC homogenous (Rf 0.45, ethyl acetate); PMR (DMSO) d 11.3 (H-N$^4$), 8.4–6.9 (H-6, H-5, Bz), 5.95 (H-1'), 5.2 (HO-3'), 3.7 (s, 6, CH$_3$O-trit.), 3.5 (s, 3, CH$_3$O-2').

Example 73

N4-Benzoyl-5'-O-(4,4'-dimethoxytriphenylmethyl)-2'-O-methyl cytidine-3'-O-β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-methylcytidine (22.0 g, 0.0333 mole) and using ethyl acetate-hexanes-triethylamine (59:40:1) as the chromatography eluent to give the product as a solid foam ( 23.6 g) in 83% yield; TLC homogenous diastereomers (Rf 0.46; 0.33, ethyl acetate-hexanes-triethylamine 59:40:1); $^{31}$P-NMR (CD$_3$CN, H$_3$PO$_4$ std.) d 150.34; 151.02 (diastereomers).

Example 74

2'-O-Nonylcytidine

Cytidine (10.1 g, 0.0415 mol), sodium hydride (2.0 g, 1.2 eq), iodononane (9.8 ml, 1.2 eq.) in DMF (100 ml) were reacted as per the procedure of Example 71, Step 1 to yield the 2' and 3' isomers as a sticky foam (11.6 g).

Example 75

N4-Benzoyl-2'-O-nonylcytidine

The mixture of 2'-O-nonylcytidine and 31-O-nonylcytidine (11.5 g) is converted to N4-benzoyl-2'-O-nonylcytidine as per the procedure of Example 71, Step 2.

Example 76

N4-Benzoyl-5'-O-(dimethoxytrityl)-2'-O-nonylcytidine

N4-Benzoyl-2'-O-nonylcytidine (2.67 g, 0.0056 mol) was treated with dimethoxytrityl chloride (2.0 g, 1.1 eq) as per the procedure of Example 72 to give 4.2 g of pure product. Anal. Calcd. for C$_{46}$H$_{53}$N$_3$O$_8$.½H$_2$O: C, 70.39; H, 6.93; N, 5.35. Found: C, 71.20; H, 6.88; N, 5.41.

Example 77

N4-Benzoyl-5'-O-(dimethoxytrityl)-2'-O-nonylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-nonylcytidine (4.1 g, 0.0053 mole) treated with bis-N,N-diisopropylaminocyanoethylphosphite (3.3 ml) and N,N-diisopropylaminohydrotetrazolide (450 mg). The product was eluted from the silica gel column using Hexane/EtOAc (3:1→1:1 with 1% triethylamine) as the chromatography eluent to give the product as a solid foam (4.21 g). $^{31}$P-NMR (CD$_3$CN, H$_3$PO$_4$ std.) shows the diastereomers;

Example 78

2'-O-Pentylcytidine

Cytidine (lo g, 0.041 mol), sodium hydride (2.4 g, 1.5 eq), bromopentane (7.6 ml, 1.5 eq.) in DMSO (90 ml) were reacted as per the procedure of Example 71, Step 1 to yield the 2' and 3' isomers as a foam (7.6 g).

Example 79

N4-Benzoyl-2'-O-pentylcytidine

The mixture of 2'-O-pentylcytidine and 3'-O-pentylcytidine (7.5 g) is converted to N4-benzoyl-2'-O-pentylcytidine as per the procedure of Example 71, Step 2.

Example 80

N4-Benzoyl-5'-O-(dimethoxytrityl)-2'-O-pentylcytidine

N4-Benzoyl-2'-O-pentylcytidine (3.0 g, 0.007 mol) was treated with dimethoxytrityl chloride (2.7 g, 1.1 eq) as per the procedure of Example 72 to give 3.5 g of pure product. Anal. Calcd. for C$_{42}$H$_{53}$N$_3$O$_8$. ½H$_2$O: C, 69.21; H, 6.36; N, 5.76. Found: C, 69.51; H, 6.30; N, 5.71.

Example 81

N4-Benzoyl-5'-O-(dimethoxytrityl)-2'-O-pentylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-pentylcytidine (3.5 g, 0.0048 mole) treated with bis-N,N-diisopropylaminocyanoethylphosphite (2.9 g, 3.1 ml, 2 eq.) and N,N-diisopropylaminohydrotetrazolide (400 mg, 0.5 eq.). The product was eluted from the silica gel column using Hexane/EtOAc (3:1→1:1 with 1triethylamine) as the chromatography eluent to give the product as a solid foam (3.24 g). $^{31}$P-NMR (CD$_3$CN, H$_3$PO$_4$ std.) shows the diastereomers.

Example 82

2'-O-Propylcytidine

Cytidine (16.5 g, 0.068 mol) was treated with sodium hydride (4.5 g) and bromopropane (15 ml) in DMF (150 ml) at room temperature for three days. The resulting reaction mixture was used directly in the next step (see Example 83).

Example 83

N4-Benzoyl-2'-O-propylcytidine

To the 2'-O-propylcytidine reaction mixture of Example 82 in an ice bath was added pyridine (60 ml) and trimethylsilyl chloride (60 ml). The reaction was stirred for 30 mins followed by the addition of benzoyl chloride (55 ml). The resulting reaction mixture was stirred for 2.5 hrs and then cooled in an ice bath. H$_2$O (100 ml) and conc. NH$_4$OH (100 ml) were added. After stirring for 30 mins, the reaction mixture was evaporated and the residue partition between H$_2$O and CH$_2$Cl$_2$. The organic phase was washed once with dil Na$_2$CO$_3$, once with dil HCl, dried over MgSO$_4$ and evaporated. The resulting residue was loaded on a silica gel column (150 g) and eluted with first CH$_2$Cl$_2$ then 5 to 10% MeOH in CH$_2$Cl$_2$ as the elution solvent. The product containing fractions were evaporated to a foam. The foam was crystallized from EtOAc/Hexanes to give the product (6.5 g total) in several crystal batches.

Example 84

N4-Benzoyl-5'-O-(dimethoxytrityl)-2'-O-propylcytidine

N4-Benzoyl-2'-O-propylcytidine (3.0 g, 0.007 mol) was treated with dimethoxytrityl chloride (1.5 g) as per the procedure of Example 72 to give 1.5 g of pure product. Anal. Calcd. for $C_{40}H_{42}N_3O_8 \cdot \frac{1}{2}H_2O$: C, 68.45; H, 6.18; N, 5.99. Found: C, 68.39; H, 5.99; N, 5.95.

Example 85

N4-Benzoyl-5'-(dimethoxytrityl)-2'-O-propylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-propylcytidine (3.8 g, 0.0055 mole) treated with bis-N,N-diisopropylaminocyanoethylphosphite (3.5 ml, 2 eq.) and N,N-diisopropylaminohydrotetrazolide (500 mg, 0.5 eq.). The product was eluted from the silica gel column using Hexane/EtOAc (1:1 with 1% triethylamine) as the chromatography eluent to give the product as a solid foam (4.72 g). $^{31}$P-NMR ($CD_3CN$, $H_3PO_4$ std.) shows the diastereomers.

Example 86

N2,N6-Diisobutyrylamino-9-(2'-O-methyl-β-D-ribofuranosyl)purine

N2,N6-Diamino-9-(2'-O-methyl-β-D-ribofuranosyl)purine (1.6 g, 5.39 mmol, see Example 34) was co-evaporated with pyridine (25 ml). A suspension of the residue in pyridine (40 ml) was cooled in an ice bath and trimethylsilyl chloride (4.8 ml) was added. The reaction mixture was stirred for 30 mins followed by the addition of butyryl chloride (2.8 ml, 5 eq). The resulting reaction mixture was stirred at room temperature for 4 hours. $H_2O$ (10 ml) and conc. $NH_4OH$ (10 ml) were added with stirring to quench the reaction mixture. After 30 mins, the reaction mixture was evaporated and the residue purified on a silica gel column using $CH_2Cl_2 \rightarrow 10\%$ MeOH/$CH_2Cl_2$ to elute the product. The appropriate fractions were evaporated to yield the product as an oil (2.4 g).

Example 87

N2,N6-Diisobutyrylamino-9-(5'-O-dimethoxytrityl-2'-O-methyl-β-D-ribofuranoayl)purine N2,N6-Diisobutyrylamino-9-(2'-O-methyl-β-D-ribofuranosyl)purine (2.4 g) was co-evaporated with pyridine and redissolved in pyridine. Dimethoxytrityl chloride (1.8 g, 1 eq) and dimethylaminopyridine (5 mg) were added and the resulting solution was stirred overnight at room temperature. The solvent was partly evaporated and the residue partition between $CH_2Cl_2$—dil. $Na_2CO_3$. The organic phase was washed with dil. $Na_2CO_3$, dried with $MgSO_4$ and evaporated. The residue was purified on a silica gel column eluted with Hexanes/EtOAc (1:1) containing 1% triethylamine. The fraction contain the product were evaporated to yield the product as a foam (2.4 g).

Example 88

N2,N6-Diisobutyrylamino-9-[5'-O-dimethoxytrityl-2'-O-methyl-3'-O-(β-cyanoethyl N,N-diisopropylphosphoramide)-β-D-ribofuranosyl] purine N2,N6-Diisobutyrylamino-9-(5'-O-dimethoxytrityl-2'-O-methyl-β-D-ribofuranosyl)purine (1.7 g, 0.0023 mol) was treated with bis-N,N-diisopropylaminocyanoethylphosphite (1.48 ml, 2 eq) and N,N-diisopropylaminohydrotetrazolide (200 mg) at room temperature overnight. The reaction mixture was partitioned between dil. $Na_2CO_3/CH_2Cl_2$, the organic phase was dried over $MgSO_4$ and evaporated. The residue was loaded on a silica gel column and eluted with Hexanes/EtOAc (3:1→1:1 with 1% triethylamine) to give the product as a solid foam (1.73 g). $^{31}$P-NMR ($CD_3CN$, $H_3PO_4$ std.) shows the diastereomers.

Example 89

Oligonucleotide Synthesis

Once nucleoside phosphoramidites of the invention have been prepared, they can then subsequently be incorporated into oligonucleotides, which are synthesized by a standard solid phase, automated nucleic acid synthesizer such as the Applied Biosystems, Incorporated 380B or MilliGen/Biosearch 7500 or 8800. Standard phosphoramidite coupling chemistries (see, e.g., M. Caruthers, *Oligonucleotides. Antisense Inhibitors of Gene Expression.*, pp. 7–24, J. S. Cohen, ed., CRC Press, Inc. Boca Raton, Fla., 1989) are used with these synthesizers to provide the desired oligonucleotides. The Beaucage reagent (see, e.g., *J. Am. Chem. Soc.* 1990, 112, 1253) or elemental sulfur (see, e.g., *Tetrahedron Letters* 1981, 22, 1859), can likewise be used to provide phosphorothioate oligonucleotides.

Example 90

A. Evaluation of the thermodynamics of hybridization of 2'-modified oligonucleotides.

The ability of the 2'-modified oligonucleotides to hybridize to their complementary RNA or DNA sequences is determined by thermal melting analysis. The RNA complement is synthesized from T7 RNA polymerase and a template-promoter of DNA synthesized with an Applied Biosystems, Inc. 380B RNA species was purified by ion exchange using FPLC (LKB Pharmacia,Inc.). Natural antisense oligonucleotides or those containing 2'-O-alkyl guanosine at specific locations are added to either the RNA or DNA complement at stoichiometric concentrations and the absorbance (260 nm) hyperchromicity upon duplex to random coil transition was monitored using a Gilford Response II spectrophotometer. These measurements are performed in a buffer of 10 mM Na-phosphate, pH 7.4, 0.1 mM EDTA, and NaCl to yield an ionic strength of 10 either 0.1 M or 1.0 M. Data is analyzed by a graphic representation of $1/T_m$ vs ln[Ct], where [Ct] was the total oligonucleotide concentration. From this analysis the thermodynamic para-meters is determined. Based upon the information gained concerning the stability of the duplex of heteroduplex formed, the placement of 2'-O-alkyl guanosine into oligonucleotides are assessed for their effects on helix stability. Modifications that drastically alter the stability of the hybrid exhibit reductions in the free energy (delta G) and decisions concerning their usefulness as antisense oligonucleotides are made.

B. Fidelity of hybridization of 2'-modified oligonucleotides

The ability of the 2'-O-alkyl guanosine modified antisense oligo-nucleotides to hybridize with absolute specificity to the targeted mRNA is shown by Northern blot analysis of purified target mRNA in the presence of total cellular RNA. Target mRNA is synthesized from a vector containing the cDNA for the target mRNA located downstream from a T7 RNA polymerase promoter. Synthesized mRNA was electrophoresed in an agarose gel and transferred to a suitable support membrane (ie. nitrocellulose). The support membrane was blocked and probed using [$^{32}$P]-labeled antisense oligonucleotides. The stringency will be determined by replicate blots and washing in either elevated temperatures or decreased ionic strength of the wash buffer. Autoradiography was performed to assess the presence of heteroduplex formation and the autoradiogram quantitated by laser densitometry (LKB Pharmacia, Inc.). The specificity of hybrid formation was determined by isolation of total cellular RNA by standard techniques and its analysis by agarose electrophoresis, embrane transfer and probing with the labeled 2'-modified oligonucleotides. Stringency was predetermined for the unmodified antisense oligonucleotides and the conditions used such that only the specifically targeted mRNA was capable of forming a heteroduplex with the 2'-modified oligonucleotide.

Example 91

Nuclease Resistance

A. Evaluation of the resistance of 2'-modified oligonucleotides to serum and cytoplasmic nucleases.

Natural phosphorothioate, and 2- modified oligonucleotides were assessed for their resistance to serum nucleases by incubation of the oligonucleotides in media containing various concentrations of fetal calf serum or adult human serum. Labeled oligonucleotides were incubated for various times, treated with protease K and then analyzed by gel electrophoresis on 20% polyacrylamine-urea denaturing gels and subsequent autoradiography. Autoradiograms were quantitated by laser densitometry. Based upon the location of the modifications and the known length of the oligonucleotide it was possible to determine the effect on nuclease degradation by the particular 2'-modification. For the cytoplasmic nucleases, a HL60 cell line was used. A postmitochondrial supernatant was prepared by differential centrifugation and the labeled oligonucleotides were incubated in this supernatant for various times. Following the incubation, oligo-nucleotides were assessed for degradation as outlined above for serum nucleolytic degradation. Autoradiography results were quantitated for comparison of the unmodified, the phosphorothioates, and the 2'-modified oligonucleotides.

B. Evaluation of the resistance of 2'-modified oligonucleotides to specific endo- and exo-nucleases.

Evaluation of the resistance of natural and 2'-modified oligonucleotides to specific nucleases (ie, endonucleases, 3',5'-exo-, and 5',3'-exonucleases) was done to determine the exact effect of the modifications on degradation. Modified oligonucleotides were incubated in defined reaction buffers specific for various selected nucleases. Following treatment of the products with proteinase K, urea was added and analysis on 20% poly-acrylamide gels containing urea was done. Gel products were visualized by staining using Stains All (Sigma Chemical Co.). Laser densitometry was used to quantitate the extend of degradation. The effects of the 2'-modifications were determined for specific nucleases and compared with the results obtained from the serum and cytoplasmic systems.

Example 92

2'-O-(nonyl)adenosine

To a solution of 10 g of adenosine in 400 ml of dimethyl formamide is added 2.25 g of 60% sodium hydride (oil). After one hour, 8.5 ml of 1-bromononane is added. The reaction is stirred for 16 hours. Ice is added and the solution evaporated in vacuo. Water and ethyl acetate are added. The organic phase is separated, dried, and evaporated in vacuo to give a white solid, which is recrystallized from ethanol to yield 4.8 g of the title compound, M.P. 143–144° C. analysis for: $C_{19}H_{31}N_5O_4$. Calculated: C, 57.99; H, 7.94; N, 1779. Found: C, 58.13; H, 7.93; N, 17.83.

Example 93

2'-O-(nonyl)-N-bensoyladenosine

2'-O-(nonyl)adenosine is treated with benzoyl chloride in a manner similar to the procedure of B. L. Gaffney and R. A. Jones, *Tetrahedron Lett.,* Vol. 23, p. 2257 (1982). After chromatography on silica gel (ethyl acetate-methanol), the title compound was obtained. Analysis for: $C_{26}H_{35}N_5O_5$. Calculated: C, 62.75; H, 7.09; N, 17.07. Found: C, 62.73; H, 14.07; N, 13.87.

Example 94

2'-O-(nonyl)-5'-O-dimethoxytrityl-$N^6$-benzoyladenosine

To a solution of 4.0 g of 2'-O-(nonyl) $N^6$-benzoyladenosine in 250 ml of pyridine is added 3.3 g of 4,4'-dimethoxytrityl chloride. The reaction is stirred for 16 hours. The reaction is added to ice/water/ethyl acetate, the organic layer is separated, dried, and concentrated in vacuo to a gum. The title compound (5.8 g) was obtained after chromatography on silica gel (ethyl acetate-methanol triethylamine). Analysis for: $C_{47}H_{53}N_5O_7$. Calculated: C, 70.56; H, 6.68; N, 8.75. Found: C, 70.26; H, 6.70; N, 8.71.

Example 95

$N^6$-benzoyl-5'-O-dimethoxytrityl-2'-O-(nonyl) adenosine-3'-O,N,N-diisopropyl-β-cyanoethyl phosphoramidite 2'-O-(nonyl)-5'-O-dimethoxytrityl-N-benzoyladenosine is treated with (β-cyanoethoxy)chloro(N,N-diisopropyl) aminephosphane in a manner similar to the procedure of F. Seela and A. Kehne, *Biochemistry,* Vol. 26, p. 2233 (1987). After chromatography on silica gel (EtOAc/hexane), the title compound was obtained as a white foam.

Example 96

2'-O-(butylphthalimide)adenomine

The title compound is prepared as per Example 92, using N-(4-bromobutyl)phthalimide instead of 1-bromononane. Chromatography on silica gel (EtOAc-MeOH) gives a white solid. M.P. 199–200° C. Analysis for: $C_{22}H_{24}N_6O_6$. Calculated: C, 56.42; H, 5.16; N, 17.94. Found: C, 56.31; H, 5.04; N, 17.95.

Example 97

2'-O-(butylphthalimide-$N^6$-benzoyladenomine)

Benzoylation of 2-O-(butylphthalimide) adenosine as per Example 93, gives the title compound. Analysis for: $C_{29}H_2N_6O_7$. Calculated: C, 60.83; H, 4.93; N, 14.68. Found: C, 60.48; N, 14.41.

Example 98

2'-O-(butylphthalimide)-5'-O-dimethoxytrityl-$N^6$-benzoyladenosine

The title compound is prepared from 2'-O-(butylphthalimide)-$N^6$-benzoyladenosine as per Example 94.

Analysis for: $C_{50}H_{46}N_6O_9$. Calculated: C, 68.64; H, 5.29; N, 9.60. Found: C, 68.47; H, 5.12; N, 9.37.

Example 99

$N^6$-benzoyl-5'-O-diethoxytrityl-2'-O-(butylphthalimide)adenosine-3'-O,N,N-diisopropyl-β-cyanoethylphophoramidine The title compound was prepared from 2'-O-(butylphthalimide)-5'-O-dimethoxytrityl-$N^6$-benzoyladenosine (from Example 98) as per Example 95. $^{31}$P NMR (CD$_3$CN) δ 150.88, 151.22.

Example 100

2'-O-[bis(phthalimidobutyl)-(aminobutyl)]-$N^6$-benzoyl-adenosine

2-O-(Butylphthalimide-$N^6$-benzoyladenosine) from Example 97 is treated with TIPS reagent (tetra-isopropyl-disilyldichloride) to block the 3',5'-hydroxyl groups with the TIPS blocking group. Treatment with ammonium hydroxide cleaves the phthalimide group yielding a 2'-O-amino butyl blocked adenosine. This compound can be further treated as per Example 96 with N-(4-bromo-butyl)phthalimide to yield the 2'-O-polyalkylamino blocked adenosine. Deblocking of the TIPS blocking group with tetrabutyl ammonium fluoride will yield the title compound. The title compound can be used as per Examples 98 and 99 to form suitable blocked nucleotides suitable for incorporation into oligonucleotides.

Example 101

Synthesis of 5LO sequence 5'-GAA GTC ACT GGA ACG-3' containing 2'-deoxy-2'-(methoxytrisethoxy)adenosine at a specific position A 0° C. solution of N6-benzoyl-3',5'-(1,1,3,3-tetraisopropyldisiloxanyl)-2'-trifluoromethylsulfonyl-9-(β-D-arabinofuranosy)adenine, methoxybisethoxyethanol and acetonitrile is treated with sodium hydride and allowed to warm to room temperature, stirred at ambient temperature for 3 hours, and then treated with tetrabutylammonium fluoride for two hours. The solution is evaporated to dryness and the residue purified by silica gel chromatography. This material is converted by procedures described above into its 5'-DMT-3'-β-cyanoethyl diisopropylphosphoramidite derivative which is inserted into the 5LO-sequence 5'-GAA GTC ACT GGA ACG via automated, solid phase DNA synthesis. Modified sequences synthesized will be:

GAa GTC ACT GGA aCG
GaA GTC ACT GGA aCG
GaA GTC aCT GGA aCG
GAA GTC aCT GGA ACG
GAA GTC ACT GGA aCG
GaA GTC ACT GGA ACG
GAA GTC ACT GGa ACG
GAa GTC ACT GGA ACG and
Gaa GTC aCT GGa aCG where a is 2'-deoxy-2'-(methoxytrisethoxy)adenosine.

What is claimed is:

1. A compound having the structure:

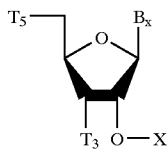

wherein:

$B_x$ is adenine, guanine, hypoxanthine, uracil, thymine, cytosine, 2-aminoadenine or 5-methylcytosine;

$T_3$ and $T_5$, independently, are OH, a nucleotide, a nucleoside, or an oligonucleotide;

X is $R_1$–$R_2$;

$R_1$ is $C_1$–$C_{20}$ alkyl; and $R_2$ is O-alkyl, S-alkyl, NH-alkyl, N-dialkyl, O-aryl, S-aryl, NH-aryl, O-aralkyl, S-aralkyl, or NH-aralkyl.

2. The compound of claim 1 wherein $R_2$ is O-alkyl.
3. The compound of claim 1 wherein $R_2$ is NH-alkyl.
4. The compound of claim 1 wherein $R_2$ is N-dialkyl.

* * * * *

UNITED STATES PATENT AND TRADEMARK OFFICE
CERTIFICATE OF CORRECTION

PATENT NO. : 5,914,396
DATED : June 22, 1999
INVENTOR(S) : Phillip Dan Cook et al.

It is certified that error appears in the above-identified patent and that said Letters Patent is hereby corrected as shown below:

Column 2,
Line 27, please delete "CH31" and insert -- $CH_3$ I --.

Column 5,
Line 63, please delete "reparation" and insert therefore -- preparation --.

Column 16,
Line 52, please delete "addition" and insert therefore -- additional --.

Column 17,
Line 36, please delete "CH3" and insert therefor -- $CH_3$ --.

Column 20,
Lines 24 and 25, please delete "CHhd2" and insert therefor -- $CH_2$ --.

Column 24,
Line 13, please delete "2' -β- (N-phthalimido) pentyl" and insert therefor -- 2' -O- (phthalimido) pentyl --.

Column 27,
Line 14, please delete "3' -βcyanoethyl" and insert therefor -- 3' -β-cyanoethyl --.

Column 32,
Line 9, please delete "1.o eq." and insert -- 3' -O- --.

Column 34,
Line 23, please delete "21,3' -dimethyl" and insert therefor -- 2',3'-dimethyl --.

Column 35,
Line 33, please delete "31-O-" and insert therefor -- -3' -O --.
Line 66, please delete "(lo g," and insert therefor -- (10 g, --.

UNITED STATES PATENT AND TRADEMARK OFFICE
CERTIFICATE OF CORRECTION

PATENT NO. : 5,914,396
DATED : June 22, 1999
INVENTOR(S) : Phillip Dan Cook et al.

It is certified that error appears in the above-identified patent and that said Letters Patent is hereby corrected as shown below:

Column 36,
Line 17, please delete "$C_{42}H_{53}N_3O_8$" and insert therefor -- $C_{42}H_{45}N_3O_8$ --.
Line 31, please delete "ltriethylamine)" and insert therefor -- 1% triethylamine) --.

Column 39,
Line 10, please delete "embrane" and insert therefor -- membrane --.

Signed and Sealed this

Seventh Day of May, 2002

Attest:

JAMES E. ROGAN
*Attesting Officer*     *Director of the United States Patent and Trademark Office*